US008921418B2

(12) United States Patent
Jenkins et al.

(10) Patent No.: US 8,921,418 B2
(45) Date of Patent: Dec. 30, 2014

(54) CONTROLLED RELEASE OF PHENOLIC OPIOIDS

(75) Inventors: Thomas E. Jenkins, Half Moon Bay, CA (US); Aleksandr Kolesnikov, San Francisco, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 67 days.

(21) Appl. No.: 13/486,613

(22) Filed: Jun. 1, 2012

(65) Prior Publication Data

US 2012/0270894 A1 Oct. 25, 2012

Related U.S. Application Data

(63) Continuation of application No. 12/302,764, filed as application No. PCT/US2007/069683 on May 24, 2007, now Pat. No. 8,217,005.

(60) Provisional application No. 60/809,082, filed on May 26, 2006, provisional application No. 60/901,795, filed on Feb. 16, 2007.

(51) Int. Cl.
| | | |
|---|---|---|
| A01N 47/10 | (2006.01) | |
| A61K 31/27 | (2006.01) | |
| C07C 261/00 | (2006.01) | |
| C07C 269/00 | (2006.01) | |
| C07C 271/00 | (2006.01) | |
| A61K 47/48 | (2006.01) | |

(52) U.S. Cl.
CPC .............................. *A61K 47/48138* (2013.01)
USPC .......................................... 514/490; 560/159

(58) Field of Classification Search
USPC .................................. 514/490; 560/156, 159
See application file for complete search history.

(56) References Cited

U.S. PATENT DOCUMENTS

| | | | |
|---|---|---|---|
| 3,927,036 | A | 12/1975 | Lee |
| 8,217,005 | B2 | 7/2012 | Jenkins et al. |
| 2004/0063628 | A1 | 4/2004 | Piccariello et al. |
| 2005/0002895 | A1 | 1/2005 | Corcoran |
| 2005/0080012 | A1 | 4/2005 | Mickle et al. |
| 2008/0207668 | A1 | 8/2008 | Moncrief |

FOREIGN PATENT DOCUMENTS

| | | |
|---|---|---|
| CA | 2497195 | 6/2003 |
| EP | 1501352 | 2/2005 |
| WO | 0332990 | 4/2003 |
| WO | 0351113 | 6/2003 |
| WO | 0372046 | 9/2003 |
| WO | 2004082620 | 9/2004 |
| WO | 2005032474 | 8/2005 |
| WO | 2006017351 | 2/2006 |
| WO | WO 2007005716 A2 * | 1/2007 |
| WO | 2007022535 | 2/2007 |
| WO | 2008157627 | 12/2008 |
| WO | 2009036322 | 3/2009 |

OTHER PUBLICATIONS

Koppert et. al., Pain, 2003, Elsevier, vol. 106, pp. 91-99.*
Portoghese et. al., Journal of Medicinal Chemistry, 1994, American Chemical Society, vol. 37, pp. 1495-1500.*
Obara et. al., British Journal of Pharmacology, 2003, Nature Publishing Group, vol. 140, pp. 538-546.*
Bennett DB (1991) "Biodegradable Polymeric Prodrugs of Naltrexone" Journal of Controlled Release, Elsevier 16 (1-2):43-52.
Bundgaard et al. (1989) "A Novel Solution-Stable, Water-Soluble Prodrug Type for Drugs Containing a Hydroxyl or an NH-Acidic Group" J. Med. Chem. 32(12):2503-2507.
De Groot, et al. (2000) "Synthesis and Biological Evaluation of 2'-Carbamate-Linked and 2'-Carbonate-Linked Prodrugs of Paclitaxel: Selective Activation by the Tumor-Associated Protease Plasmin" J. Med. Chem. 43 (16):3093-3102.
De Groot, et al. (2001) "Elongated Multiple Electronic Cascade and Cyclization Spacer Systems in Activatible Anticancer Prodrugs for Enhanced Drug Release" J. Org Chem. 66(26):8815-8830.
Dhareshwar & Stella (2007) Biotechnology: Pharmaceutical Aspects: Prodrugs of Alcohols and Phenols Springer New York, vol. 5 (Part 3.2):63-99.
Fredholt Thomsen et al. (1993) "Cyclization-Activated Phenyl Carbamate Prodrug Forms for Protecting Phenols against First-Pass Metabolism" Int. J Pharm. 91:39-49.
Gomes et al. (2007) "Cyclization-Activated Prodrugs" Molecules 12:2484-2506.
Hamad et al. (2006) "Synthesis and Hydrolytic Behavior of Two Novel Tripartite Codrugs of Naltrexone and 6beta-Naltrexol with Hydroxybupropion as Potential Alcohol Abuse and Smoking Cessation Agents" Bioorganic & Medicinal Chemistry 14(20):7051-7061.
Hay et al. (1968) "Catalysis by Aromatic Aldehydes and Carbon Dioxide of the Hydrolysis of the P-Nitrophenyl Esters of L-Leucine, Glycine, and L-B-Phenylalanine" Hydrolysis of Nitrophenyl Esters: 155-169.
Jensen et al. (1991) "Water-Soluble Aminoalkylbenzoate Esters of Phenols as Prodrugs: Synthesis, Enzymatic Hydrolysis and Chemical Stability of Paracetamol Esters" Acta. Pharm. Nord. 3(1):31-40.
Kovach (1975) "Amino Acid Esters of Phenolic Drugs as Potentially Useful Prodrugs" J. Pharm. Sci. 64(6):1071-1072.
Page et al. (1986) "Stereochemical Studies. Part 112: Geometrical Dependence of Intramolecular Catalysis in the Hydrolysis and Aminolysis of Aryl Esters" J. Chem. Soc. Perkin. Trans. 2:867-871.
Patani & Lavoie (1996) "Bioisosterism: A Rational Approach in Drug Design" Chem. Rev. 96:3147-3176.

(Continued)

*Primary Examiner* — Sarah Pihonak
(74) *Attorney, Agent, or Firm* — Carol L. Francis; Khin K. Chin; Bozicevic, Field & Francis LLP

(57) ABSTRACT

A method of providing a patient with controlled release of a phenolic opioid using a prodrug capable, upon enzymatic activation, of releasing the phenolic opioid through intramolecular cyclization leading to formation of a cyclic urea, carbamate or thiocarbamate.

18 Claims, 1 Drawing Sheet

(56) References Cited

OTHER PUBLICATIONS

Saari et al. (1990) "Cyclization-Activated Prodrugs. Basic Cabamates of 4-Hdroxyanisole" Journal of Medicinal Chemistry 33(1):97-101.

Testa (Ed.) "Chapter 8: The hydrolysis of carboxylic acid ester prodrugs" Hydrolysis in Drug and Prodrug Metabolism, Verlag Helvetica Chimica Acta, 419-514, (2003).

Thomsen et al. (1994) "Evaluation of Phenyl Carbamates of Ethyl Diamines as Cyclization-Activated Prodrug Forms for Protecting Phenols against First-Pass Metabolism" Int. J. Pharma. 112:143-152.

Valters (1982) "The Electronic and Steric Effects in Heterolytic Intramolecular Cyclisation Reactions" Russian Chemical Reviews 51(8):788-801.

Vigroux et al. (1995) "Cyclization-Activated Prodrugs: N-(Substituted 2-Hydroxyphenyl and 2-Hydroxypropyl) Carbamates Based on Ring-Opened Derivatives of Active Benzoxazolones and Oxazolidinones as Mutual Prodrugs of Acetaminophen" J. Med. Chem. 38:3983-3994.

Wermuth (1996) "Designing Prodrugs and Bioprecursors I: Carrier Prodrugs," The Practice of Medicinal Chemistry, Academic, London: 671-696.

* cited by examiner

CONTROLLED RELEASE OF PHENOLIC OPIOIDS

This application is a continuation of U.S. patent application Ser. No. 12/302,764 filed on Jun. 9, 2009, which is a National Stage application under 35 U.S.C. §371 of International Application No. PCT/US2007/069683 filed on May 24, 2007 and claims benefit of U.S. provisional patent application No. 60/809,082 filed on May 26, 2006 and U.S. provisional patent application No. 60/901,795 filed on Feb. 16, 2007, the contents of which are incorporated herein in their entirety.

The present invention relates to controlled release of phenolic opioids. More particularly it relates to a method of providing patients with controlled release of phenolic opioids using prodrugs having a particular substituent on the phenolic hydrogen atom, to prodrugs of phenolic opioids and to pharmaceutical compositions comprising the prodrugs.

Delivery systems are often essential in safely administering active agents such as drugs. Often delivery systems can optimize bioavailability, improve dosage consistency and improve patient compliance (e.g., by reducing dosing frequency). Solutions to drug delivery and/or bioavailability issues in pharmaceutical development include converting known drugs to prodrugs. Typically, in a prodrug, a polar functional group (e.g., a carboxylic acid, an amino group, phenol group, a sulfhydryl group, etc.) of the active agent is masked by a promoiety, which is labile under physiological conditions. Accordingly, prodrugs are usually transported through hydrophobic biological barriers such as membranes and may possess superior physicochemical properties in comparison to the parent drug. Prodrugs are usually non-toxic and are ideally electively cleaved at the locus of drug action. Preferably, cleavage of the promoiety occurs rapidly and quantitatively with the formation of non-toxic by-products (i.e., the hydrolyzed promoiety).

Prodrugs as described above are capable of providing patients with safe and effective treatment if the patients follow the directions given by the attending physician. Unfortunately human patients do not always follow the directions that they have been given. They may accidentally take an overdose of the prodrug, or deliberately abuse it, for example by taking an overdose, by injecting or inhaling it, or by using readily available household chemicals (like vinegar or baking soda) to obtain the active drug from the prodrug. Abuse is a particular concern with prodrugs of opioids, which are properly used for the treatment of pain.

It would be desirable to have a prodrug of an opioid that has built-in control, so that it is difficult to use the prodrug other than in the way it is intended.

A way has now been found for configuring prodrugs of phenolic opioids that affords controlled release of the drugs.

Phenolic opioids form a sub-group of the opioids, and include the widely prescribed drugs hydromorphone, oxymorphone, and morphine.

According to one aspect, the present invention provides a method of providing a patient with post administration-activated, controlled release of a phenolic opioid, which comprises administering to said patient a corresponding compound in which the phenolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, carbamate to or thiocarbamate, liberating the compound from the spacer leaving group so as to provide the patient with controlled release of the phenolic opioid.

In another aspect, the present invention provides the use in the manufacture of a medicament for providing a patient with post administration-activated, controlled release of a phenolic opioid, of a corresponding compound in which the phenolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, carbamate or thiocarbamate, liberating the compound from the spacer leaving group so as to provide the patient with controlled release of the phenolic opioid.

The corresponding compound (prodrug in accordance with the present invention) provides post administration-activated, controlled release of the phenolic opioid, because it requires enzymatic cleavage to initiate release of the compound, and because the rate of release of the opioid depends upon both the rate of enzymatic cleavage and the rate of cyclisation. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic-cleavage.

The enzyme capable of cleaving the enzymatically-cleavable moiety may be a peptidase—the enzymatically-cleavable moiety being linked to the nucleophilic nitrogen through an amide (e.g. a peptide: —NHCO—) bond. In some embodiments, the enzyme is a digestive enzyme such as, for example, pepsin, trypsin, chymotrypsin, colipase, elastase, aminopeptidase N, aminopeptidase A, dipeptidylaminopeptidase IV, tripeptidase or enteropeptidase. Accordingly, in one embodiment of the method, the corresponding compound is administered orally to the patient.

The enzyme-cleavable moiety linked to the nitrogen nucleophile through an amide bond may be, for example, a residue of an amino acid or a peptide, or an (alpha) N-acyl derivative of an amino acid or peptide (for example an N-acyl derivative of a pharmaceutically acceptable carboxylic acid, such as an N-acetyl derivative). The peptide may contain, for example, up to 10 amino acid residues. For example, it may be a dipeptide or tripeptide. Each amino acid may advantageously be a naturally occurring D or L-amino acid (such as an L-amino acid). Examples of naturally occurring amino acids are alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine. Accordingly, examples of enzyme-cleavable moieties include residues of the L-amino acids listed hereinabove and the N-acetyl derivatives thereof, and dipeptides and tripeptides formed from two or three of the L-amino acids listed hereinabove, and the N-acetyl derivatives thereof.

The cyclic group formed when the phenolic opioid is released is conveniently pharmaceutically acceptable, in particular a pharmaceutically acceptable cyclic urea, carbamate or thiocarbamate. It will be appreciated that cyclic ureas in particular are generally very stable and have low toxicity.

In one specific example of the invention, the spacer leaving group bearing a nucleophile that is protected with a cleavable moiety is a group of formula —C(O)—N(CH$_3$)—(CH$_2$)$_2$—NH(R$^4$) wherein R$^4$ is an enzyme-cleavable moiety linked to the NH group through an amide bond. When the N—R$^4$ amide bond is cleaved enzymatically, a nitrogen nucleophile (—NH$_2$) is freed, and this cyclises back onto the carbonyl group, forming a cyclic urea and releasing the phenolic opioid.

Generally, the spacer group may be any group capable of forming a cyclic urea, carbamate or thiocarbamate when the phenolic opioid is displaced by the nitrogen nucleophile. Accordingly, the spacer group may be, for example, a group of formula —C(O)—Y-L-N—(R$^3$)(R$^4$); in which:—

Y is —NR$^5$—, —O— or —S—;

L is an unsubstituted or substituted alkyl, alkenyl, alkynyl, carbocyclic or heterocyclic group, or a combination of two or more such groups linked together by a single bond, a spiro linkage, a single or double bond or by a C=O, O, S, SO, SO$_2$, CONN, NHCO or NH linkage;

each of R$^3$ and R$^5$ is independently is hydrogen, alkyl, substituted alkyl, aryl or substituted aryl; and R$^4$ is an enzyme-cleavable moiety linked to the nitrogen of the N(R$^3$) group through an amide bond.

In one embodiment, R$^4$ is a group of formula

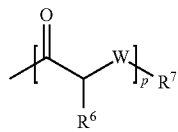

wherein:

each R$^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^6$ and R$^7$ together with the atoms to which they are bonded form a cycloheteroalkyl or substituted cycloheteroalkyl ring;

R$^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —NR$^8$—, —O— or —S—; and each R$^8$ is independently hydrogen, alkyl, substituted alkyl, aryl or substituted aryl, or optionally, each R$^6$ and R$^8$ independently together with the atoms to which they are bonded form a cycloheteroalkyl or substituted cycloheteroalkyl ring.

It will be appreciated that when W is NH and R$^7$ is H or acyl, then R$^4$ is a residue of an amino acid or peptide, or an N-acyl derivative thereof. When W is NR$^8$, R$^7$ is H or acyl and R$^6$ and R$^8$ together with the atoms to which they are bonded form a pyrrolidine ring, then R$^4$ is a residue of proline or an N-acyl derivative thereof.

Accordingly, in another embodiment, R$^4$ is a residue of a D or L-amino acid (such as an L-amino acid) selected from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; a residue of a dipeptide or tripeptide composed of two or three D or L amino acid residues (such as L-amino acid residues) selected independently from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; or a residue of an N-acyl derivative thereof, such as an N-acetyl derivative.

In one embodiment, L is an unsubstituted or substituted 1,2-phenylene group. For example, Y-L-NR$^3$ together may form a 1,2-diaminophenylene group which is unsubstituted or substituted on the phenylene moiety with one or two substituents selected from a halogen atom, (1-4C)alkyl and (1-4C)alkoxy.

In another embodiment, L is a divalent group of formula

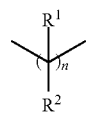

in which:— n is an integer from 1 to 10; and each of R$^1$ and R$^2$ is independently hydrogen, alkyl, substituted alkyl, aryl or substituted aryl, or R$^1$ and R$^2$ together with the carbon to which they are attached form a cycloalkyl or substituted cycloalkyl group, or two R$^1$ or R$^2$ groups on adjacent carbon atoms may, together with the carbon atoms to which they are attached, form a cycloalkyl or substituted cycloalkyl group.

Accordingly, in one embodiment, the spacer leaving group bearing a nucleophile that is protected with a cleavable moiety is of formula —C(O)—Y—(C(R$^1$)(R$^2$))$_n$—N—(R$^3$)(R$^4$); the spacer leaving group corresponding with the group —C(O)—Y—(C(R$^1$)(R$^2$))$_n$—, the nucleophilic nitrogen atom that is protected with a cleavable moiety corresponding with the group —N—(R$^3$)(R$^4$) and the cleavable moiety corresponding with the group R$^4$; in which:

Y is —NR$^5$—, —O— or —S—;

n is an integer from 1 to 10;

each R$^1$, R$^2$, R$^3$ and R$^5$ is independently hydrogen, alkyl, substituted alkyl, aryl or substituted aryl, or R$^1$ and R$^2$ together with the carbon to which they are attached form a cycloalkyl or substituted cycloalkyl group, or two R$^1$ or R$^2$ groups on adjacent carbon atoms may, together with the carbon atoms to which they are attached, form a cycloalkyl or substituted cycloalkyl group;

R$^4$ is

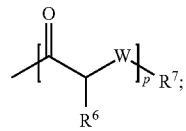

each R$^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, R$^6$ and R$^7$ together with the atoms to which they are bonded form a cycloheteroalkyl or substituted cycloheteroalkyl ring;

R$^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 5;

each W is independently —NR$^8$—, —O— or —S—; and each R$^8$ is independently hydrogen, alkyl, substituted alkyl, aryl or substituted aryl, or optionally, each R$^6$ and R$^8$ independently together with the atoms to which they are bonded form a cycloheteroalkyl or substituted cycloheteroalkyl ring.

Thus, if XH represents the phenolic opioid that is released, then the corresponding compound may be represented by the general formula (I)

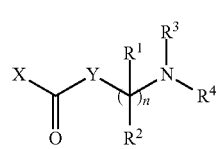

(I)

and the cyclic urea, carbamate or thiocarbamate may be presented by the formula

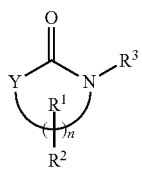

In one embodiment, each of $R^1$, $R^2$, $R^3$ and $R^5$ is independently hydrogen, alkyl, substituted alkyl, aryl or substituted aryl.

In another embodiment, $R^6$ is a side atom or group of a natural amino acid, such as H (from glycine), —$CH_2$ ($CH_2$)$_3NH_2$ (from leucine), —$CH_2CH_2CH_2NHC(NH)NH_2$ (from arginine), 4-hydroxybenzyl (from tyrosine), $CH_2COOH$ (from aspartic acid) or $CH_2CH_2COOH$ (from glutamic acid).

In another embodiment, $R^7$ is a hydrogen atom, or an unsubstituted of substituted acyl group, for example (1-6C) alkanoyl, such as acetyl or t-butanoyl; benzoyl unsubstituted or substituted by methylenedioxy or one or two substituents selected from (1-4C)alkyl, (1-4C)alkoxy or halogen, such as benzoyl or piperonyl; $CONR_xR_y$ in which $R_x$ and $R_y$ are each independently hydrogen or (1-4C)alkyl, such as $CONH_2$), or a hemiacid or hemiester, such as $CH_2CH_2COOH$ or $CH_2CH_2COOEt$. The unsubstituted of substituted acyl group is conveniently the residue of a pharmaceutically acceptable carboxylic acid.

Examples of particular values are:—
for Y: —$NR^5$;
for $R^5$: (1-4C)alkyl, such as —$CH_3$;
for L: —$CH_2CH_2$
for $R^1$ and $R^2$: hydrogen or (1-4C)alkyl, such as $CH_3$; more particularly hydrogen;
for n: 2 or 3;
for $R^3$: hydrogen or (1-4C)alkyl, such as —$CH_3$;
for W: NH;
for $R^6$: H, —$CH_2(CH_2)_3NH_2$, —$CH_2CH_2CH_2NHC(NH)NH_2$, 4-hydroxybenzyl, $CH_2COOH$ or $CH_2CH_2COOH$;
for $R^7$: hydrogen, (1-6C)alkanoyl, such as acetyl or t-butanoyl, or optionally substituted benzoyl, for example benzoyl unsubstituted or substituted by methylenedioxy or one or two substituents selected from (1-4C)alkyl, (1-4C)alkoxy or halogen, such as benzoyl or piperonyl; in particular hydrogen or acetyl;
for a cycloheteroalkyl or substituted cycloheteroalkyl ring formed by $R^6$ and $R^8$ together with the atoms to which they are bonded: pyrrolidinyl;
for p: 1 or 2;
for $R^4$: arginine, N-acetylarginine, N-t-butanoylarginine, N-benzoylarginine, N-piperonylarginine, N-glycinylarginine, lysine, glutamic acid, aspartic acid, tyrosine, proline and N-glycinylproline.

Generally the corresponding compound (the prodrug in accordance with the invention) is administered orally. However, in certain embodiments it is envisaged that it could be administered by another route.

Each corresponding compound may have a different release profile, the rate of release of the phenolic opioid depending upon the rate at which the cleavable moiety is cleaved, and the rate in which the nitrogen nucleophile can undergo an intramolecular cyclization—release reaction thus displacing the phenolic opioid. Accordingly, one embodiment of the method comprises administering a plurality of corresponding compounds to the patient, each corresponding compound having a different spacer leaving group and/or a different cleavable moiety so as to provide the patient with a different controlled release of the phenolic opioid.

Specific examples of phenolic opioids include oxymorphone, hydromorphone, morphine and derivatives thereof. Particular mention is made of oxymorphone, hydromorphone and morphine. Other examples of phenolic opioids are buprenorphine, dihydroetorphine, diprenorphine, etorphine and levorphanol.

The prodrugs may be administered alone or may be co-administered with one or more other active agents. In one embodiment, they may be co-administered with a peripheral opioid antagonist, such as (R)—N-methylnaltrexone (N-MTX), or a pro-drug thereof. It will be appreciated by those skilled in the art that (R)—N-methylnaltrexone antagonizes the actions of opioids such as hydromorphone, oxymorphone and morphine, but is incapable of crossing the blood brain barrier. It therefore antagonizes only their peripheral actions, which are undesirable, not their actions on the central nervous system, such as pain relief, which are desirable. In one embodiment, the pro-drug of (R)—N-methylnaltrexone is a compound of formula (I) in which X represents the phenolic residue of (R)—N-methylnaltrexone, Y, $R^1$, $R^2$, n, $R^3$ have any of the meanings given hereinabove, and $R^4$ is hydrogen or has any of the meanings given hereinabove. Such a pro-drug may be administered orally. Compounds in which $R^4$ has any of the meanings given above desirably release (R)—N-methylnaltrexone in the way that the pro-drug of the opioid releases the opioid it is being used to antagonize. Such compounds may be formulated for co-administration with a pro-drug of an opioid according to the present invention, for example in a pharmaceutical composition comprising both compounds and a pharmaceutically acceptable carrier. It will be appreciated that the parent drug, (R)—N-methylnaltrexone has poor oral bioavailability, and generally needs to be administered parenterally. Thus, the pro-drugs of (R)—N-methylnaltrexone in accordance with the present invention are useful whenever oral (R)—N-methylnaltrexone therapy is desired.

In another aspect, the present invention provides a prodrug of oxymorphone, hydromorphone or morphine that is capable of providing post administration-activated controlled release of oxymorphone, hydromorphone or morphine. Accordingly, the present invention provides a compound of structural Formula (I):

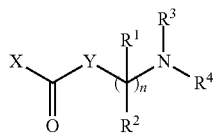

(I)

or a salt, hydrate or solvate thereof wherein:

X is oxymorphone, hydromorphone or morphine, wherein the hydrogen atom of the phenolic hydroxyl group is replaced by a covalent bond to —C(O)—Y—(C($R^1$)($R^2$))$_n$—N—($R^3$)($R^4$);

Y is —$NR^5$—, —O— or —S—;

n is an integer from 1 to 4;

each $R^1$, $R^2$, $R^3$ and $R^5$ is independently hydrogen, alkyl, substituted alkyl, aryl or substituted aryl, or $R^1$ and $R^2$ together with the carbon to which they are attached form a cycloalkyl or substituted cycloalkyl group, or two $R^1$ or $R^2$ groups on adjacent carbon atoms may, together with the carbon atoms to which they are attached, form a cycloalkyl or substituted cycloalkyl group;

$R^4$ is

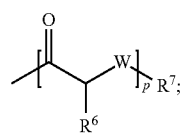

each $R^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^6$ and $R^7$ together with the atoms to which they are bonded form a cycloheteroalkyl or substituted cycloheteroalkyl ring;

$R^7$ is hydrogen, alkyl, substituted alkyl, acyl, substituted acyl, alkoxycarbonyl, substituted alkoxycarbonyl, aryl, substituted aryl, arylalkyl or substituted arylalkyl;

p is an integer from 1 to 10;

each W is independently —$NR^8$—, —O— or —S—; and each $R^8$ is independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

For example, when X is a residue of hydromorphone, the compound of formula (I) has the structure

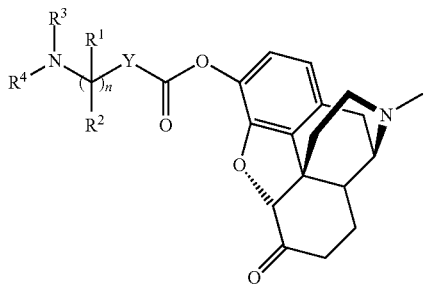

In one embodiment, X is hydromorphone or oxymorphone. In another embodiment, X is morphine.

In another aspect the present invention provides a compound of formula I

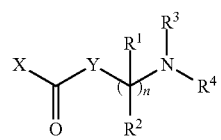

(I)

or a salt, hydrate or solvate thereof wherein:

X is (R)—N-methylnaltrexone, wherein the hydrogen atom of the phenolic hydroxyl group is replaced by a covalent bond to —C(O)—Y—(C($R^1$)($R^2$))$_n$—N—($R^3$)($R^4$); and Y, $R^1$, $R^2$, n, $R^3$ and $R^4$ have any of the meanings given hereinabove.

In another aspect, pharmaceutical compositions are provided which generally comprise one or more compounds of Formula (I), salts, hydrates or solvates thereof and a pharmaceutically acceptable vehicle such as a diluent, carrier, excipient or adjuvant. The choice of diluent, carrier, excipient and adjuvant will depend upon, among other factors, the desired mode of administration.

In still another aspect, methods for treating or preventing various diseases or disorders are provided. The methods generally involve administering to a patient in need of such treatment or prevention a therapeutically effective amount of a compound Formula (I) and/or a pharmaceutical composition thereof.

Figure 1:
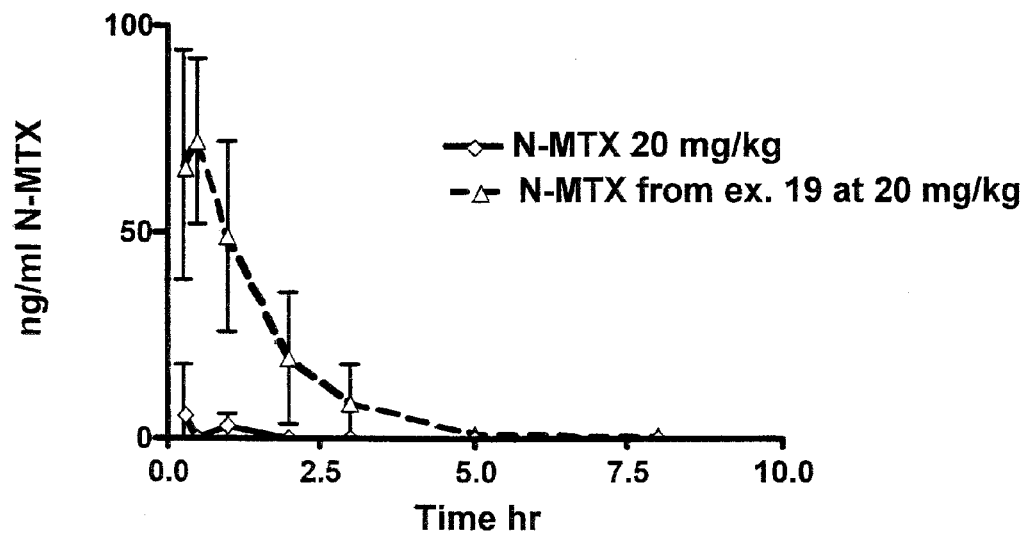
FIG. 1 shows the plasma concentration time course of the production of N-MTX following oral (PO) dosing in rats.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl; propyls such as propan-1-yl or propan-2-yl; and butyls such as butan-1-yl, butan-2-yl, 2-methyl-propan-1-yl or 2-methyl-propan-2-yl.

In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, t-butanoyl, cyclohexylcarbonyl, cyclohexylmethylcarbonyl, benzoyl, piperonyl, benzylcarbonyl and the like.

"Alkoxy" by itself or as part of another substituent refers to a radical —O$R^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)O$R^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms. In other embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenyleth-1-yl, naphthylmethyl, 2-naphthyleth-1-yl, naphthobenzyl, 2-naphthophenyleth-1-yl and the like. In some embodiments, an arylalkyl group is ($C_7$-$C_{30}$) arylalkyl, e.g., the alkyl moiety of the arylalkyl group is ($C_1$-$C_{10}$) and the aryl moiety is ($C_6$-$C_{20}$). In other embodiments, an arylalkyl group is ($C_7$-$C_{20}$) arylalkyl, e.g., the alkyl moiety of the arylalkyl group is ($C_1$-$C_8$) and the aryl moiety is ($C_6$-$C_{12}$).

Compounds may be identified either by their chemical structure and/or chemical name. The compounds described herein may contain one or more chiral centers and/or double bonds and therefore, may exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms. Certain compounds may exist in multiple crystalline or amorphous forms. In general, all physical forms are equivalent for the uses contemplated herein and are intended to be within the scope of the present disclosure.

"Cycloalkyl" by itself or as part of another substituent refers to a saturated cyclic alkyl radical. Typical cycloalkyl groups include, but are not limited to, groups derived from cyclopropane, cyclobutane, cyclopentane, cyclohexane and the like. In some embodiments, the cycloalkyl group is ($C_3$-$C_{10}$) cycloalkyl. In other embodiments, the cycloalkyl group is ($C_3$-$C_7$) cycloalkyl.

"Cycloheteroalkyl" by itself or as part of another substituent, refers to a saturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkenyl and Heteroalkynyl" by themselves or as part of another substituent refer to alkyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —N$R^{37}R^{38}$—, =N—N=, —N=N—, —N=N—N$R^{39}R^{40}$, —P$R^{41}$—, —P(O)$_2$—, —PO$R^{42}$—, —O—P(O)$_2$—, —SO—, —SO$_2$—, —Sn$R^{43}R^{44}$— and the like, where $R^{37}$, $R^{38}$, $R^{39}$, $R^{40}$, $R^{41}$, $R^{42}$, $R^{43}$, and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, to isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5-20 membered heteroaryl. In other embodiments, the heteroaryl group is from 5-10 membered heteroaryl. In still other embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. In some embodiments, the heteroarylalkyl group is a 6-30 membered heteroarylalkyl, e.g., the alkyl moiety of the heteroarylalkyl is 1-10 membered and the heteroaryl moiety is a 5-20-membered heteroaryl. In other embodiments, the heteroarylalkyl group is 6-20 membered heteroarylalkyl, e.g., the alkyl moiety of the heteroarylalkyl is 1-8 membered and the heteroaryl moiety is a 5-12-membered heteroaryl.

"Opioid"—refers to a chemical substance that exerts its pharmacological action by interaction at opioid receptors, providing patients with relief from pain. "Phenolic opioid" refers to a subset of the opioids that contains a phenol group. Examples of phenolic opioids include buprenorphine, dihydroetorphine, diprenorphine, etorphine, hydromorphone, levorphanol, morphine, and oxymorphone. An "opioid antagonist" is a compound that antagonizes the pharmacological action of an opioid. The term includes phenolic opioid antagonists. Examples of phenolic opioid antagonists include naltrexone, naloxone, and (R)—N-methylnaltrexone. A "peripheral opioid antagonist" is a compound that is not capable of penetrating the blood/brain barrier, and hence is capable of antagonizing the (undesired) action of an opioid outside the central nervous system. An example of a peripheral phenolic opioid antagonist is (R)—N-methylnaltrexone.

"Parent Aromatic Ring System" by itself or as part of another substituent, refers to an unsaturated cyclic or polycyclic ring system having a conjugated 7C electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutical composition" refers to at least one compound and a pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with, or in which a compound is administered.

"Patient" includes mammal humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of an active agent that requires a transformation within the body to release the active agent. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, $C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In some embodiments, substituents include -M, —$R^{60}$, =O, —$OR^{60}$, —$SR^{60}$, —$S^-$, =S, —$NR^{60}R^{61}$, =$NR^{60}$, —$CF_3$, CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In other embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In still other embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to various embodiments. It will be understood that the invention is not limited to these embodiments. To the contrary, it is intended to cover alternatives, modifications, and equivalents as may be included within the spirit and scope of the allowed claims.

Disclosed herein are prodrugs of phenolic opioids. The promoiety of the prodrug includes a spacer group and a cleavable moiety where the spacer group, inter alia, physically separates the drug from the cleavable moiety. Accordingly, a prodrug disclosed herein comprises a phenol attached through the phenolic oxygen to a spacer, which is further attached to a cleavable moiety. Cleavage of the cleavable moiety reveals a nucleophilic nitrogen resulting in the "activation" of the prodrug. The controlled release of the parent drug can now be mediated by the nucleophilic nitrogen undergoing an intramolecular cyclization-release reaction.

The cleavable moiety may comprise an amide. Generally, the cleavable moiety can be cleaved under physiological conditions. The cleavable moiety is cleaved enzymatically.

In some embodiments, a compound of structural Formula (I) or salts, solvates or hydrates thereof is provided

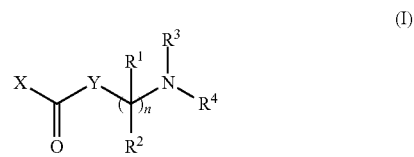

(I)

wherein:
X is a phenolic opioid, wherein the hydrogen atom of the hydroxyl group is replaced by a covalent bond to —C(O)—Y—(C($R^1$)($R^2$))$_n$—N—($R^3$)($R^4$);
Y is —$NR^5$—, —O— or —S—;
n is an integer from 1 to 4;
each $R^1$, $R^2$, $R^3$ and $R^5$ is independently hydrogen, alkyl, substituted alkyl, aryl or substituted aryl, or $R^1$ and $R^2$ together with the carbon to which they are attached form a cycloalkyl or substituted cycloalkyl group;
$R^4$ is

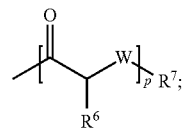

each $R^6$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^6$ and $R^7$ together with the atoms to which they are bonded form a cycloheteroalkyl or substituted cycloheteroalkyl ring;
$R^7$ is hydrogen, alkyl, substituted alkyl, acyl, substituted acyl, alkoxycarbonyl, substituted alkoxycarbonyl, aryl, substituted aryl, arylalkyl or substituted arylalkyl;
p is an integer from 1 to 10;
each W is independently —$NR^8$—, —O— or —S—; and
each $R^8$ is independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In some embodiments, each of $R^1$, $R^2$, $R^3$ and $R^5$ is independently hydrogen, alkyl, substituted alkyl, aryl or substituted aryl.

In some embodiments, X is hydromorphone, morphine or oxymorphone. In other embodiments, X is buprenorphine, dihydroetorphine, diprenorphine, etorphine or levorphanol.

In some embodiments, $R^7$ is hydrogen, alkyl, acyl or alkoxycarbonyl. In other embodiments, $R^7$ is

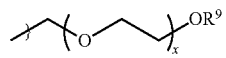

where $R^9$ is hydrogen or alkyl and x is an integer between 1 and 2000. In other embodiments, $R^7$ is a commercially available PEG derivative such as, for example, PEG-200, PEG-400, PEG-1550, PEG-3350, PEG-6000, PEG-20,000 or PEG-40,000.

In some embodiments, Y is $NR^5$ and $R^5$ is hydrogen or alkyl. In other embodiments, n is 2 or 3. In other embodiments, n is 1. In still other embodiments, $R^1$, $R^2$, $R^3$, $R^5$ and $R^8$ are independently hydrogen or alkyl.

In some embodiments, each $R^6$ is independently, hydrogen, alkyl, substituted alkyl, aryl, arylalkyl, cycloalkyl, substituted cycloalkyl, substituted arylalkyl or heteroarylalkyl or optionally, $R^6$ and $R^7$ together with the atoms to which they are attached form a cycloheteroalkyl or substituted cycloheteroalkyl ring. In other embodiments, $R^6$ is independently hydrogen, alkyl, substituted alkyl, aryl, arylalkyl, substituted arylalkyl, heteroalkyl, heteroarylalkyl, substituted heteroarylalkyl, or optionally, $R^6$ and $R^7$ together with the atoms to which they are bonded form a cycloheteroalkyl or substituted cycloheteroalkyl ring. In still other embodiments, each $R^6$ is independently, hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5-dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4-dichlorobenzyl, 3,4 dichlorobenzyl, 3,4 difluorobenzyl, 3,5 diiodo-4-hydroxylbenzyl, 3-nitro-4-hydroxybenzyl, aminomethyl,

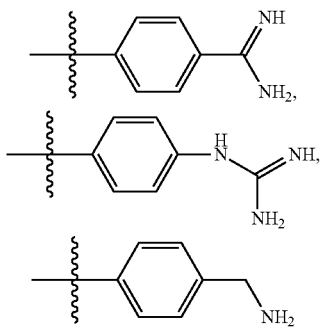

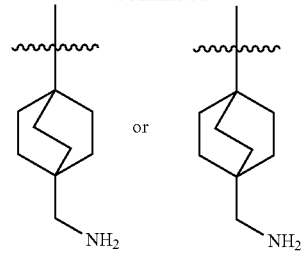

or optionally $R^6$ and $R^7$ together with the atoms to which they are attached form an azetidine, pyrrolidine or piperidine ring.

In some embodiments, W is —$NR^8$ and each $R^7$ is independently hydrogen or alkyl, aryl or arylalkyl.

In some embodiments, $R^7$ is hydrogen, alkyl, acyl or alkoxycarbonyl.

In other embodiments, each $R^6$ is independently —$CH_2(CH_2)_3NH_2$ or —$CH_2CH_2CH_2NHC(NH)NH_2$. In still other embodiments, p is 1 and $R^6$ is —$CH_2(CH_2)_3NH_2$ or —$CH_2CH_2CH_2NHC(NH)NH_2$. In still other embodiments, each W is —$NR^8$—, each $R^8$ is hydrogen and $R^7$ is hydrogen, acyl, substituted acyl, alkoxycarbonyl or substituted alkoxycarbonyl.

In some embodiments, each $R^6$ is independently phenyl, benzyl, 4-hydroxybenzyl, 4-bromobenzyl, 4-imidazolylmethyl, 3-indolylmethyl, isobutyl, —$CH_2CH_2SCH_3$, —$CH_2CH_2CONH_2$, —$CH_2CH_2CONH_2$ or —$CH_2CO_2H$. In still other embodiments, each $R^6$ is independently benzyl, 4-hydroxybenzyl, 4-bromobenzyl or 3-indolylmethyl. In still other embodiments, n is 1 and $R^6$ is phenyl, benzyl, 4-hydroxybenzyl, 4-bromobenzyl, 4-imidazolylmethyl, 3-indolylmethyl, isobutyl, —$CH_2CH_2SCH_3$, —$CH_2CH_2CONH_2$, —$CH_2CH_2CONH_2$ or —$CH_2CO_2H$. In still other embodiments, n is 1 and $R^6$ is benzyl, 4-hydroxybenzyl, 4-bromobenzyl or 3-indolylmethyl. In some of any of the above embodiments, each W is —$NR^8$—, each $R^8$ is hydrogen and $R^7$ is acyl, substituted acyl, alkoxycarbonyl or substituted alkoxycarbonyl.

In some embodiments, p is greater than 1 and $R^7$ is hydrogen. In any of the above embodiments, each W is —$NR^8$—, each $R^8$ is hydrogen and $R^7$ is acyl, substituted acyl, alkoxycarbonyl or substituted alkoxycarbonyl.

In some embodiments, p is 3 and $R^7$ is hydrogen. In other embodiments, each W is —$NR^8$— and each $R^8$ is hydrogen.

In some embodiments, each $R^6$ is independently hydrogen, methyl, isopropyl, isobutyl, sec-butyl, —$CH_2OH$ or —$CH_2SH$. In other embodiments, p is 1 and $R^6$ is hydrogen, methyl, isopropyl, isobutyl or sec-butyl, each W is —$NR^8$—, each $R^8$ is hydrogen and $R^7$ is acyl, substituted acyl, alkoxycarbonyl or substituted alkoxycarbonyl.

In some embodiments, each $R^6$ is independently hydrogen, methyl, isopropyl, isobutyl, sec-butyl, t-butyl, cyclopentyl, cyclohexyl, —$CH_2OH$, —$CH(OH)CH_3$, —$CH_2CONH_2$, —$CH_2CH_2SCH_3$, —$CH_2SH$, phenyl, benzyl, 4-hydroxybenzyl, 4-bromobenzyl or 3-indolylmethyl. In other embodiments, each $R^6$ is independently hydrogen, methyl, isopropyl, isobutyl, sec-butyl, t-butyl, cyclopentyl, cyclohexyl, phenyl, benzyl, 4-bromobenzyl, 3-indolylmethyl or optionally $R^6$ and $R^7$ together with the atoms to which they are attached form an azetidine, pyrrolidine or piperidine ring. In some of the above embodiments, each W is —$NR^8$—, each $R^8$ is hydrogen or optionally each $R^6$ and $R^8$, independently together with the atoms to which they are attached form an azetidine, pyrrolidine or piperidine ring and $R^7$ is acyl, substituted acyl, alkoxycarbonyl or substituted alkoxycarbonyl.

In some embodiments, each $R^6$ is independently benzyl, 4-hydroxybenzyl or isobutyl. In other embodiments, each W is —$NR^8$—, each $R^8$ is hydrogen and $R^7$ is acyl, substituted acyl, alkoxycarbonyl or substituted alkoxycarbonyl.

In some embodiments, each $R^6$ is independently —$CH_2CO_2H$ or —$CH_2CH_2CO_2H$. In other embodiments, each W is —$NR^8$—, each $R^8$ is hydrogen and $R^7$ is acyl, substituted acyl, alkoxycarbonyl or substituted alkoxycarbonyl.

In some embodiments, p is 2 and the $R^6$ group adjacent to the N-terminal nitrogen atom is independently, hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl (phenethyl), 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5-dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4-dichlorobenzyl, 3,4 dichlorobenzyl, 3,4 difluorobenzyl, 3,5 diiodo-4-hydroxylbenzyl, 3-nitro-4-hydroxybenzyl, aminomethyl,

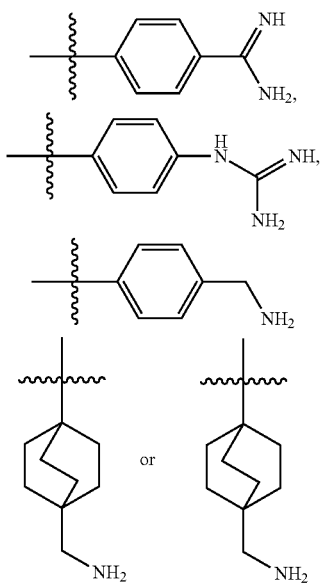

or optionally each $R^6$ and $R^8$, independently together with the atoms to which they are attached form an azetidine, pyrrolidine or piperidine ring and the other $R^6$ group is methyl or $R^6$ and $R^8$, independently together with the atoms to which they are attached form a pyrrolidine ring. In other embodiments, each W is —$NR^8$—, each $R^8$ is hydrogen or optionally each $R^6$ and $R^8$, independently together with the atoms to which they are attached form a pyrrolidine ring and $R^7$ is acyl, substituted acyl, alkoxycarbonyl or substituted alkoxycarbonyl.

In some of the above embodiments, p is 1, and $R^6$ is hydrogen. In some of the above embodiments, p is 1, $R^6$ is hydrogen and W is NH. In some of the above embodiments, p is 1, $R^6$ is hydrogen, W is NH and $R^7$ is hydrogen. In other embodiments, each $R^6$ is hydrogen and W is NH. In still other embodiments, each $R^6$ is hydrogen, W is NH and $R^7$ is hydrogen.

In some embodiments, Y is $NR^5$, n is 2 or 3, p is 1 or 2, $R^1$, $R^2$, $R^3$, $R^5$ and $R^7$ are independently hydrogen or alkyl, each $R^6$ is independently hydrogen, alkyl, substituted alkyl, aryl, arylalkyl, substituted arylalkyl, heteroalkyl, heteroarylalkyl, substituted heteroarylalkyl or optionally, $R^6$ and $R^7$ together with the atoms to which they are bonded form a cycloheteroalkyl or substituted cycloheteroalkyl ring. In other embodiments, Y is $NR^5$, n is 2, p is 1, $R^1$ and $R^2$ are hydrogen, $R^3$ and $R^5$ are methyl or hydrogen and $R^6$ is independently hydrogen, alkyl, substituted alkyl, aryl, arylalkyl, substituted arylalkyl, heteroalkyl, heteroarylalkyl, substituted heteroarylalkyl or optionally, $R^6$ and $R^7$ together with the atoms to which they are bonded form a cycloheteroalkyl or substituted cycloheteroalkyl ring or optionally $R^7$ is hydrogen. In still other embodiments, Y is $NR^5$, n is 2, $R^1$ and $R^2$ are hydrogen, $R^3$ and $R^5$ are methyl or hydrogen, $R^7$ is hydrogen and $R^6$ is —$CH_2(CH_2)_3NH_2$ or —$CH_2CH_2CH_2NHC(NH)NH_2$. In some of the above embodiments, X is oxymorphone or hydromorphone.

The compounds described herein may be obtained via the routes generically illustrated in Schemes 1-4.

The promoieties described herein, may be prepared and attached to drugs containing phenols by procedures known to those of skill in the art (See e.g., Green et al., "Protective Groups in Organic Chemistry," (Wiley, $2^{nd}$ ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, (Wiley Interscience); Trost et al., "Comprehensive Organic Synthesis," (Pergamon Press, 1991); "Theilheimer's Synthetic Methods of Organic Chemistry," Volumes 1-45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well established synthetic procedures, supra.

Scheme 1

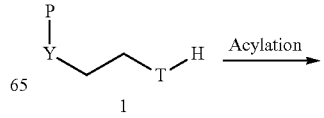

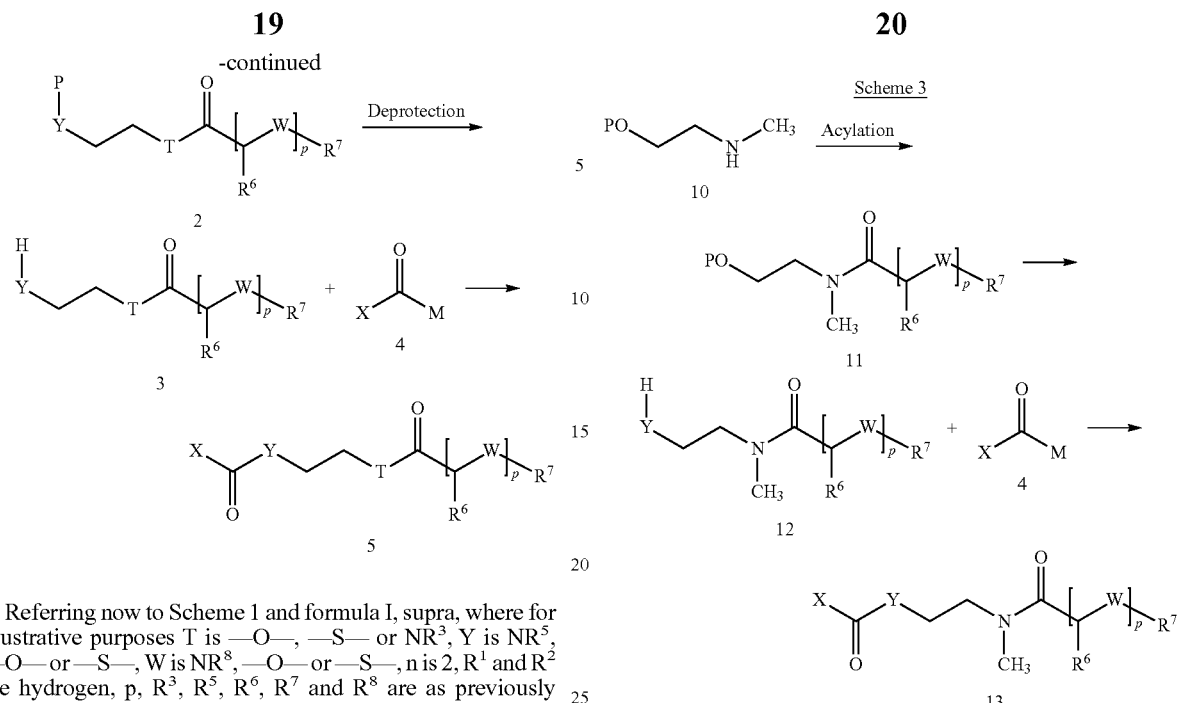

Referring now to Scheme 1 and formula I, supra, where for illustrative purposes T is —O—, —S— or $NR^3$, Y is $NR^5$, —O— or —S—, W is $NR^8$, —O— or —S—, n is 2, $R^1$ and $R^2$ are hydrogen, p, $R^3$, $R^5$, $R^6$, $R^7$ and $R^8$ are as previously defined, X is a phenolic opioid, P is a protecting group, and M is a leaving group, compound 1 may be acylated with an appropriate carboxylic acid or carboxylic acid equivalent to provide compound 2 which then may be deprotected to yield compound 3. Compound 3 is then reacted with an activated carbonic acid equivalent 4 to provide desired compound 5.

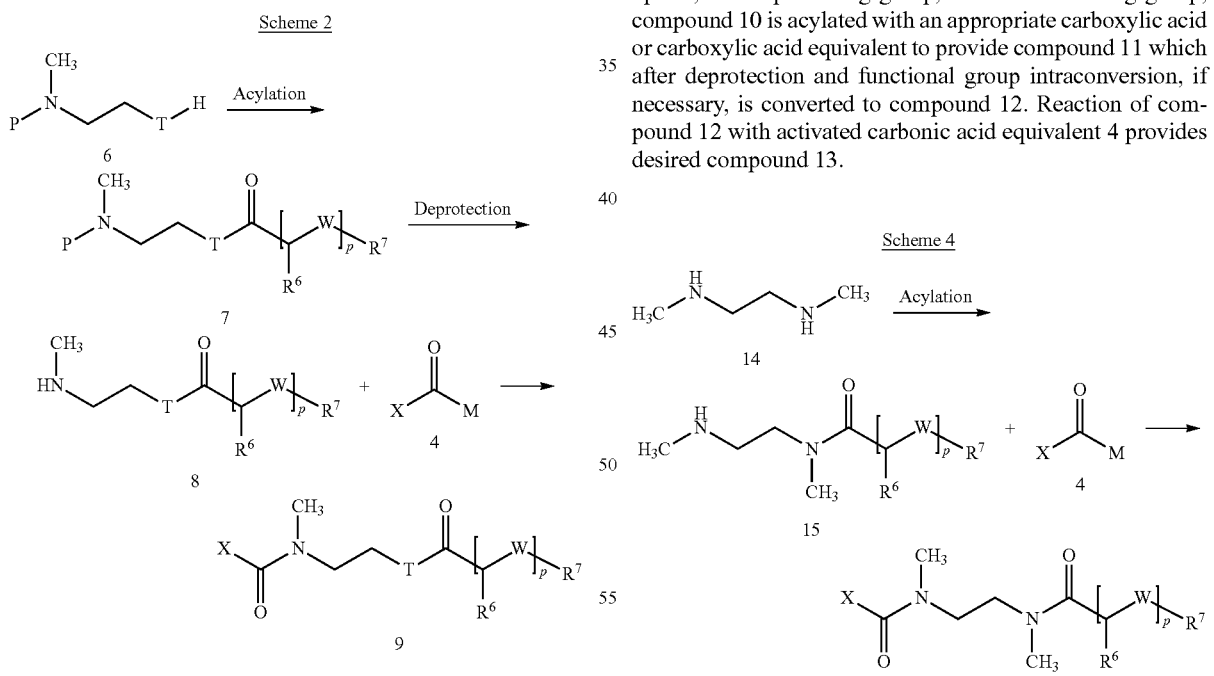

Referring now to Scheme 2 and formula I, supra, where for illustrative purposes T is —O—, —S— or $NR^3$, Y is $NCH_3$, W is $NR^8$, —O— or —S—, n is 2, $R^1$ and $R^2$ are hydrogen, p, $R^3$, $R^6$, $R^7$ and $R^8$ are as previously defined, X is a phenolic opioid, P is a protecting group, and M is a leaving group, compound 6 is acylated with an appropriate carboxylic acid or carboxylic acid equivalent to provide compound 7. Compound 7 is then deprotected and reacted with activated carbonic acid equivalent 4 to provide desired compound 9.

Referring now to Scheme 3 and formula I, supra, where for illustrative purposes T is $NCH_3$, Y is $NR^5$, —O— or —S—, W is $NR^8$, —O— or —S—, n is 2, $R^1$ and $R^2$ are hydrogen, p, $R^5$, $R^6$, $R^7$ and $R^8$ are as previously defined, X is a phenolic opioid, P is a protecting group, and M is a leaving group, compound 10 is acylated with an appropriate carboxylic acid or carboxylic acid equivalent to provide compound 11 which after deprotection and functional group intraconversion, if necessary, is converted to compound 12. Reaction of compound 12 with activated carbonic acid equivalent 4 provides desired compound 13.

Referring now to Scheme 4 and formula I, supra, where for illustrative purposes T and Y are $NCH_3$, W is $NR^8$, —O— or —S—, n is 2, $R^1$ and $R^2$ are hydrogen, p, $R^6$, $R^7$ and $R^8$ are as previously defined, X is a phenolic opioid, P is a protecting group, and M is a leaving group, compound 14 is acylated with an appropriate carboxylic acid or carboxylic acid equivalent to provide compound 15. Reaction of compound 15 with activated carbonic acid equivalent 4 provides desired compound 16.

A compound of formula (I) so prepared in which $R^7$ represents a hydrogen atom may then be further acylated to afford a corresponding compound of formula (I) in which the value of p has been increased, or in which $R^7$ represents an acyl group.

According to another aspect, therefore, the present invention provides a process for the preparation of a compound of formula (I) or a pharmaceutically acceptable salt thereof, which comprises reacting a compound of formula (III)

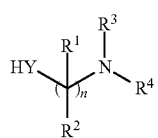
(III)

or a protected derivative thereof, with a compound of formula (IV)

(IV)

in which M represents a leaving atom or group, such as an activated aryloxycarbonyl group, for example p-nitrophenoxycarbonyl;

followed by removing any protecting groups and, if desired, acylating a compound of formula (I) in which $R^7$ (in the group $R^4$ as defined hereinabove) represents a hydrogen atom and/or forming a pharmaceutically acceptable salt.

Compounds of formula (I) in which X represents a residue of (R)—N-methylnaltrexone can also be prepared by methylating a corresponding compound of formula (I) in which X is a residue of naltrexone, or a protected derivative thereof.

Selection of appropriate protecting groups, reagents and reaction conditions for any of the steps in the above Schemes is well within the ambit of those of skilled in the art. Other methods for synthesis of the prodrugs described herein will be readily apparent to the skilled artisan and may be used to synthesize the compounds described herein. Accordingly, the methods presented in the Schemes herein are illustrative rather than comprehensive.

The invention further provides all the novel intermediates described herein.

In general, the prodrugs disclosed herein may be used to treat and/or prevent the same disease(s) and/or conditions as the parent drug which are well known in the art (see, e.g., Physicians Desk Reference, 2000 54$^{th}$ Edition and the Merck Index, 13$^{th}$ Edition). Phenolic opioids are useful in the treatment of pain.

For example, a prodrug of a phenolic opioid such as hydromorphone could be used, inter alia, to treat or prevent pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The pharmaceutical compositions disclosed herein comprise a prodrug disclosed herein with a suitable amount of a pharmaceutically acceptable vehicle, so as to provide a form for proper administration to a subject.

Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compositions and compounds disclosed herein into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions or any other form suitable for use known to the skilled artisan. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995).

Pharmaceutical compositions for oral delivery may be in the form of tablets, lozenges, aqueous or oily suspensions, granules, powders, emulsions, capsules, syrups, slurries, suspensions or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, sucrose, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), granulating agents, binding agents and disintegrating agents such as the cross-linked polyvinylpyrrolidone, agar, or alginic acid or a salt thereof such as sodium alginate etc.

In some embodiments, pharmaceutical compositions are in the form of lozenges or lollipops where dissolution and release of the active ingredients occurs in the oral cavity, generally through the oral mucosa. For these embodiments, buffering agents may also be used to provide an optimum environment for delivery of the agents or compositions. Additional components may include, for example, sweeteners, binders, diluents, disintegrating agents, lubricating agents, etc.

In still other embodiments, the pharmaceutical composition is a dissolving sublingual tablet, where dissolution and release of the active ingredients occurs under the tongue, and the compositions and/or compounds disclosed herein are absorbed through the oral mucosa. In these embodiments, buffering agents may also be used to provide an optimum environment for delivery of each of the agents. Additional components may include, for example, sweeteners, binders, diluents, disintegrating agents, etc.

The methods that involve oral administration of compounds disclosed herein of can also be practiced with a number of different dosage forms, which provide sustained release.

In some embodiments, the dosage form is comprised of beads that on dissolution or diffusion release compositions and/or compounds disclosed herein over an extended period of hours, preferably, over a period of at least 6 hours, more preferably, over a period of at least 8 hours and even more preferably, over a period of at least 12 hours and most preferably, over a period of at least 24 hours. The beads may have a central composition or core comprising compounds disclosed herein and pharmaceutically acceptable vehicles, including optional lubricants, antioxidants and buffers. The beads may be medical preparations with a diameter of about 1 to about 2 mm. Individual beads may comprise doses of the compounds disclosed herein. The beads, in some embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, *Int. J. Pharm.* 1994, 112, 117-124; Pharmaceutical Sciences by Remington, 14$^{th}$ ed, pp 1626-1628 (1970); Fincher, *J. Pharm. Sci.* 1968, 57, 1825-1835; Benedikt, U.S. Pat. No. 4,083,949) as has the manufacture of tablets (Pharmaceutical Sciences, by Remington, 17$^{th}$ Ed, Ch. 90, pp 1603-1625 (1985).

In other embodiments, an oral sustained release pump may be used (Langer, supra; Sefton, 1987, *CRC Crit. Ref Biomed. Eng.* 14:201; Saudek et al., 1989, *N. Engl. J Med.* 321:574).

In still other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; Levy et al., 1985, *Science* 228: 190; During et al., 1989, *Ann. Neurol.* 25:351; Howard et al., 1989, *J. Neurosurg.* 71:105). In some embodiments, polymeric materials are used for oral sustained release delivery. Such polymers include, for example, sodium carboxymethylcellulose, hydroxypropylcellulose, hydroxypropylmethylcellulose and hydroxyethylcellulose (most preferred, hydroxypropylmethylcellulose). Other cellulose ethers have been described (Alderman, Int. *J. Pharm. Tech. & Prod. Mfr.* 1984, 5(3) 1-9).

Factors affecting drug release are well known to the skilled artisan and have been described in the art (Bamba et al., *Int. J. Pharm.* 1979, 2, 307).

In still other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. For example, solid microparticles of compositions and/or compounds disclosed herein may be coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained releasing waxes are disclosed in Cain et al., U.S. Pat. No. 3,402,240 (carnauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., *Drug Dev. Ind. Pharm.* 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In yet other embodiments, a controlled-release system can be placed in proximity of the target of the compositions and/or compounds disclosed herein thus requiring only a fraction of the systemic dose (See, e.g., Goodson, in "Medical Applications of Controlled Release," supra, vol. 2, pp. 115-138 (1984)). Other controlled-release systems are discussed in Langer, 1990, *Science* 249:1527-1533 may also be used.

In still other embodiments, the dosage form comprises compounds disclosed herein coated on a polymer substrate. The polymer can be an erodible or a nonerodible polymer. The coated substrate may be folded onto itself to provide a bilayer polymer drug dosage form. For example, compounds disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the compounds over a sustained release period. Representative biodegradable polymers comprise a member selected from the group consisting of biodegradable poly(amides), poly (amino acids), poly(esters), poly (lactic acid), poly(glycolic acid), poly(carbohydrate), poly (orthoester), poly (orthocarbonate), poly(acetyl), poly (anhydrides), biodegradable poly(dihydropyrans), and poly (dioxinones) which are known in the art (Rosoff, *Controlled Release of Drugs*, Chap. 2, pp. 53-95 (1989); Heller et al., U.S. Pat. No. 3,811,444; Michaels, U.S. Pat. No. 3,962,414;

Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises compounds disclosed herein loaded into a polymer that releases the drug(s) by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of the drug(s). The dosage form may be manufactured by procedures known in the art. An example of providing a dosage form comprises blending a pharmaceutically acceptable carrier like polyethylene glycol, with a known dose of compositions and/or compounds disclosed herein at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., *Polymers* 1990, 31, 1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; Chien et al., U.S. Pat. No. 3,992,518).

In other embodiments, the dosage form comprises a plurality of tiny pills. The tiny time-release pills provide a number of individual doses for providing various time doses for achieving a sustained-release drug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix comprises a plurality of 4 to 50 tiny pills, each tiny pill comprises a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of drug(s). Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising compounds disclosed herein. In use within a subject, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of compounds disclosed herein present in the compartment, a drug-containing layer composition in the compartment, a hydrogel push layer composition in the compartment comprising an osmotic formulation for imbibing and absorbing fluid for expanding in size for pushing the drug composition layer from the dosage form, and at least one passageway in the wall for releasing the composition. The method delivers compounds disclosed herein by imbibing fluid through the semipermeable wall at a fluid imbibing rate determined by the permeability of the semipermeable wall and the osmotic pressure across the semipermeable wall causing the push layer to expand, thereby delivering the compounds disclosed herein from the dosage form through the exit passageway to a subject over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycoumarin, butylated hydroxytoluene, cephalm, ethyl gallate, propyl gallate, octyl gallate, lauryl gallate, propylhydroxybenzoate, trihydroxybutyrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid and a fatty, alicyclic or aromatic acid.

In the osmotic dosage forms, the semipermeable wall comprises a composition that is permeable to the passage of fluid and impermeable to the passage of compounds disclosed herein. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkylcellulose such as hydroxypropylmethylcellulose. The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of compounds disclosed herein to a subject over time. The dosage form comprises a passageway in the wall that connects the exterior of the dosage form with the internal compartment. The osmotic powered dosage form can be made to deliver drug from the dosage form to the subject at a zero order rate of release over a period of up to about 24 hours.

The expression "passageway" as used herein comprises means and methods suitable for the metered release of the compounds disclosed herein from the compartment of the dosage form. The exit means comprises at least one passageway, including orifice, bore, aperture, pore, porous element, hollow fiber, capillary tube, channel, porous overlay, or porous element that provides for the osmotic controlled release of the compounds disclosed herein. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly (lactic) acid polymer in the wall, a gelatinous filament, poly (vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of compositions and/or drugs from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et al., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the subject and increase subject compliance, the sustained release oral dosage form (regardless of the specific form of the sustained release dosage form) preferably, provides therapeutic concentrations of the compounds disclosed herein in the patient's blood over a period of at least about 6 hours, more preferably, over a period of at least about 8 hours, even preferably, over a period of at least about 12 hours and most preferably, over a period of at least 24 hours.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Liquid drug formulations suitable for use with nebulizers and liquid spray devices and EHD aerosol devices will typically include compounds disclosed herein with a pharmaceutically acceptable carrier such as, for example, a liquid (e.g., alcohol, water, polyethylene glycol or a perfluorocarbon). Optionally, another material may be added to alter the aerosol properties of the solution or suspension of compositions and/or compounds disclosed herein. In some embodiments, this material is liquid such as an alcohol, glycol, polyglycol or a fatty acid. Other methods of formulating liquid drug solutions or suspension suitable for use in aerosol devices are known to those of skill in the art (Biesalski, U.S. Pat. No. 5,112,598; Biesalski, U.S. Pat. No. 5,556,611).

For topical administration a compound disclosed herein may be formulated as solutions, gels, ointments, creams, suspensions, etc. as are well-known in the art.

For buccal administration, the compounds disclosed herein may take the form of tablets, lozenges, lollipops, etc. formulated in a conventional manner.

Compounds disclosed herein may also be formulated in rectal or vaginal compositions such as suppositories or retention enemas, e.g., containing conventional suppository bases such as cocoa butter or other glycerides.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include but are not limited to sodium channel blockers, antibiotics, N-acetyl cysteine, homocysteine and phospholipids.

For injection, compounds disclosed herein may be formulated in aqueous solutions, such as physiologically compatible buffers such as Hanks' solution, Ringer's solution, physiological saline buffer or in association with a surface-active agent (or wetting agent or surfactant) or in the form of an emulsion (as a water-in-oil or oil-in-water emulsion). Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent may comprise between 0.05 and 5% surface-active agent or between 0.1 and 2.5% surface-active agent. The solution may contain formulatory agents such as suspending, stabilizing and/or dispersing agents. Alternatively, compounds disclosed herein may be in powder form for constitution with a suitable vehicle, e.g., sterile pyrogen-free water, before use.

Suitable emulsions may be prepared using commercially available fat emulsions. The combination (or single components) may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. In some embodiments, EDTA is added as a preservative.

In addition to the formulations described previously, compounds disclosed herein may also be formulated as a depot preparation. Such long acting formulations may be administered by implantation (for example, subcutaneously or intramuscularly) or by intramuscular injection. Thus, for example, compounds disclosed herein may be formulated with suitable polymeric or hydrophobic materials (for example, as an emulsion in an acceptable oil) or ion exchange resins, or as sparingly soluble derivatives, for example, as a sparingly soluble salt.

When used to treat and/or prevent diseases the compounds disclosed herein and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions. The specific pharmaceutical composition depends on the desired mode of administration, as is well known to the skilled artisan.

Compounds disclosed herein and/or pharmaceutical compositions thereof may be administered to a subject by intravenous bolus injection, continuous intravenous infusion, oral tablet, oral capsule, oral solution, intramuscular injection, subcutaneous injection, transdermal absorption, buccal absorption, intranasal absorption, inhalation, sublingual, intracerebrally, intravaginally, rectally, topically, particularly to the ears, nose, eyes, or skin or any other convenient method known to those of skill in the art. In some embodiments, compounds disclosed herein and/or pharmaceutical compositions thereof are delivered via sustained release dosage forms, including oral sustained release dosage forms. Administration can be systemic or local. Various delivery systems are known, (e.g., encapsulation in liposomes, microparticles, microcapsules, capsules, "patient controlled analgesia" drug delivery systems, etc.) that can be used to deliver compounds disclosed herein and/or pharmaceutical compositions thereof.

Compounds disclosed herein and/or pharmaceutical compositions thereof may also be administered directly to the lung by inhalation. For administration by inhalation, the compounds disclosed herein and/or pharmaceutical compositions thereof may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver the compounds disclosed herein and/or pharmaceutical compositions thereof.

Alternatively, a Dry Powder Inhaler ("DPI") device may be used to administer compounds disclosed herein and/or pharmaceutical compositions thereof (See, e.g., Raleigh et al., *Proc. Amer. Assoc. Cancer Research Annual Meeting*, 1999, 40, 397). DPI devices typically use a mechanism such as a burst of gas to create a cloud of dry powder inside a container, which may then be inhaled by the patient. A popular variation is the multiple dose DPI ("MDDPI") system, which allows for the delivery of more than one therapeutic dose. For example, capsules and cartridges of gelatin for use in an inhaler or insufflator may be formulated containing a powder mix of the compositions and/or compounds disclosed herein and a suitable powder base such as lactose or starch for these systems.

Another type of device that may be used to deliver the compounds disclosed herein and/or pharmaceutical compositions thereof is a liquid spray device supplied, for example, by Aradigm Corporation, Hayward, Calif. Liquid spray systems use extremely small nozzle holes to aerosolize liquid drug formulations that may then be directly inhaled.

In some embodiments, a nebulizer device is used to deliver compounds and/or pharmaceutical compositions thereof disclosed herein. Nebulizers create aerosols from liquid drug formulations by using, for example, ultrasonic energy to form fine particles that may be readily inhaled (e.g., Verschoyle et al., *British J. Cancer*, 1999, 80, Suppl. 2, 96; Armer et al., U.S. Pat. No. 5,954,047; van der Linden et al., U.S. Pat. No. 5,950, 619; van der Linden et al., U.S. Pat. No. 5,970,974).

In still other embodiments, an electrohydrodynamic ("EHD") aerosol device is used to deliver the compounds disclosed herein and/or pharmaceutical compositions thereof. EHD aerosol devices use electrical energy to aerosolize liquid drug solutions or suspensions (see e.g., Noakes et al., U.S. Pat. No. 4,765,539; Coffee, U.S. Pat. No. 4,962, 885; Coffee, International Publication No. WO 94/12285; Coffee, International Publication No. WO 94/14543; Coffee, International Publication No. WO 95/26234; Coffee, International Publication No. WO 95/26235; Coffee, International Publication No. WO 95/32807). Other methods of intra-pulmonary delivery of a compound disclosed herein and/or pharmaceutical composition thereof are known to the skilled artisan and are within the scope of the present disclosure.

Transdermal devices can also be used to deliver the compounds disclosed herein and/or pharmaceutical compositions thereof. In some embodiments, the transdermal device is a matrix type transdermal device (Miller et al., International Publication No. WO 2004/041324). In other embodiments, the transdermal device is a multi-laminate transdermal device (Miller, United States Patent Application Publication No. 2005/0037059).

The amount of compounds disclosed herein and/or pharmaceutical compositions thereof that will be effective in the treatment or prevention of diseases in a patient will depend on the specific nature of the condition and can be determined by standard clinical techniques known in the art. The amount of compounds disclosed herein and/or pharmaceutical compositions thereof administered will, of course, be dependent on, among other factors, the subject being treated, the weight of the subject, the severity of the affliction, the manner of administration and the judgment of the prescribing physician.

In certain embodiments, compounds disclosed herein and/ or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent (e.g. including, but not limited to, peripheral opioid antagonists, laxatives, non-opioid analgesics and the like). In other embodiments, compounds disclosed herein and/or pharmaceutical compositions thereof are administered prior or subsequent to administration of other therapeutic agents.

In one embodiment, the present invention provides a pharmaceutical composition comprising a compound of Formula (I), or a salt, hydrate of solvate thereof, in which X is (R)—N-methylnaltrexone and a compound of Formula (I), or a salt, hydrate of solvate thereof, in which X is a phenolic opioid, such as oxymorphone, hydromorphone or morphine, and a pharmaceutically acceptable carrier.

It will be apparent to those skilled in the art that many modifications, both to materials and methods, may be practiced without departing from the scope of this disclosure. Accordingly, the present embodiments are to be considered as illustrative and not restrictive, and the invention is not to be limited to the details given herein, but may be modified within the scope and equivalents of the allowed claims.

All publications and patents cited herein are incorporated by reference in their entirety.

The following examples illustrate the invention.

In the examples, the following abbreviations are used:—

HOBt: 1-Hydroxybenzotriazole; PyBOP: Benzotriazole-1-yl-oxy-tris-pyrrolidino-phosphonium hexafluorophosphate; DIEA: diisopropylethylamine; and BocGlyOSu: N—(N-alpha-glycinyloxy)succinimide.

Preparation 1

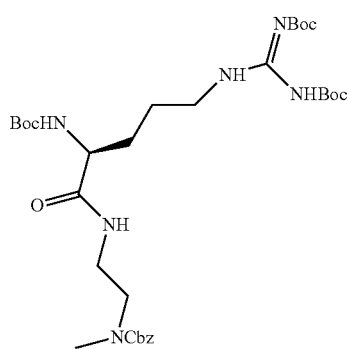

BocArg(diBoc)OH (Bachem, 0.47 g, 1.0 mmol) was dissolved in dimethylformamide (5 ml) and mixed with HOBt (0.15 g (1.15 mmol) and PyBOP (0.6 g, 1.15 mmol). Diisopropylethylamine (0.4 ml, 2.3 mmol) was added to the mixture, then the resulting solution was stirred for 10 minutes and added to a solution of $H_2NCH_2CH_2N(CH_3)CBz$ (0.28 g, 1.15 mmol) in dimethylformamide (3 ml). The basicity was adjusted by addition of DIEA (0.4 ml (2.3 mmol). The mixture was stirred for 2 hours and then poured into 40 ml of 5% aqueous citric acid. The product was extracted with a 20 ml of ethyl ether and ethyl acetate (5:1). The organic layer was washed with water, two times with 10 ml of 1M aqueous sodium carbonate, water and brine, and then dried over magnesium sulfate. The solvents were removed by evaporation to afford 0.65 g (98%) of depicted product.

Preparation 2

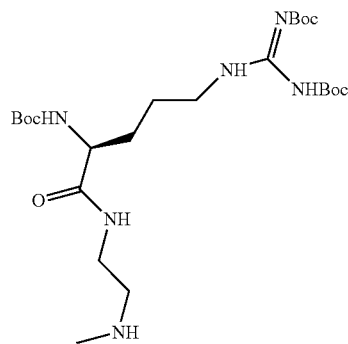

The product of Preparation 1 (0.65 g, 0.98 mmol) was dissolved in ethanol (10 ml). Pearlman's catalyst (0.32 g) was then added and the mixture was subjected to hydrogenation (1 atm, 24 h). The resultant mixture was then filtered from the catalyst and the solvent was removed by evaporation. The residue was further dried under high vacuum for 2 hours to afford 0.525 g (99%) of the depicted product.

Preparation 3

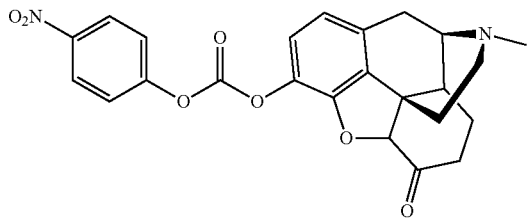

Hydromorphone (0.21 g (0.74 mmol) was suspended in dichloromethane (3 ml). p-Nitrophenylchlorocarbonate (0.16 g (0.79 mmol) in dichloromethane (3 ml) was then added dropwise over a period of 5 minutes. The reaction mixture was then sonicated for 2 hours to afford a stock solution of the depicted product that was used in the next step.

Preparation 4

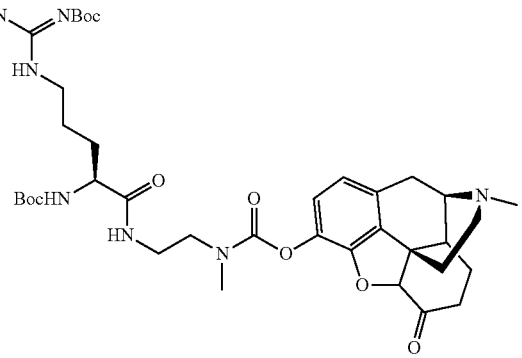

The product of Preparation 2 (0.21 g, 0.38 mmol) was added to the product of Preparation 3 (stock solution, 3 ml, 0.38 mmol). The pH was then adjusted by adding triethylamine (0.056 ml, 0.4 mmol). The reaction mixture was then stirred for 6 hours. The solvent was then evaporated under a vacuum, and the residue was dissolved in a diethyl ether-ethyl acetate mixture (3:1, 10 ml) and washed four times with 5 ml of 1M aqueous sodium carbonate. The organic layer was then washed three times with water (10 ml) and once with brine (10 ml), then dried over magnesium sulfate. The solvent was then removed by evaporation to afford the depicted product 0.28 g (87.5%).

EXAMPLE 1

Hydromorphone 3-(N-methyl-N-(2-arginylamino))ethylcarbamate

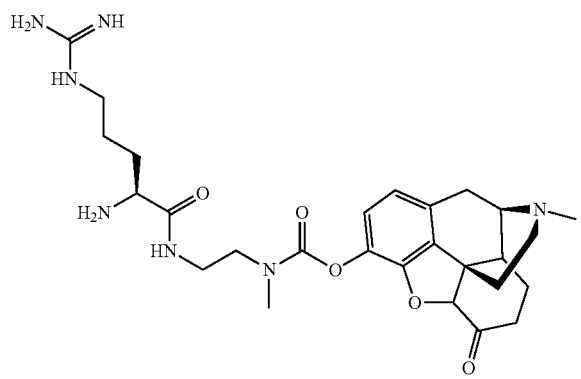

The product of Preparation 4 (0.28 g, 0.33 mmol) was dissolved in a 1:1 mixture of dichloromethane and trifluoroacetic acid (6 ml). The reaction mixture was then stirred for 6 hours. The solvent was then removed by evaporation under a vacuum, and the residue was triturated with ethyl ether (10 ml). A precipitate formed, and this was filtered off, washed with diethyl ether (10 ml) four times and dried in a stream of dry nitrogen gas to afford a crude product (0.26 g). A portion of the crude product (0.14 g) was purified by reverse phase preparative HPLC (acetonitrile gradient) to afford the depicted compound (0.031 g, 29%). Mass spec: Calculated 541.3. Observed 542.4

Preparation 5

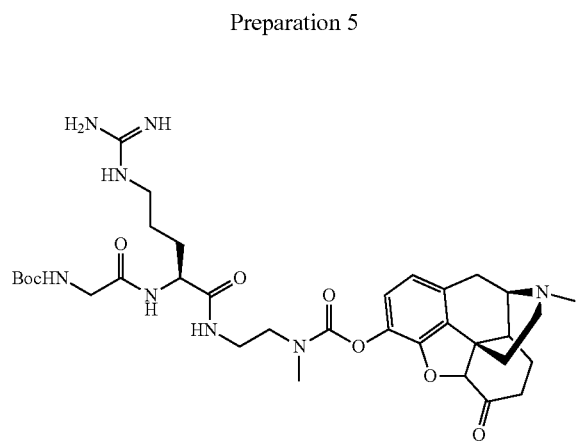

BocGlyOSu (0.037 g, 0.136 mmol) was added to a stirred solution of the product of Example 1 (0.12 g, 0.136 mmol) in dimethylformamide (3 ml). Triethylamine (0.048 ml, 0.272) mmol) was then added to the reaction mixture and the resulting solution was stirred for 2 hours. The solvent was then removed by evaporation under a high vacuum, and the residue was triturated with diethyl ether (3 ml) to afford the depicted compound (0.125 g, 100%).

EXAMPLE 2

Hydromorphone 3-(N-methyl-N-(2-N'-glycinylarginylamino))ethylcarbamate

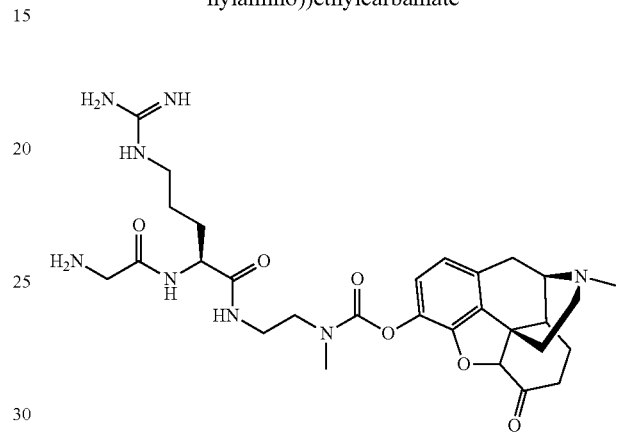

The product of Preparation 5 was deprotected following the method of Example 1 to afford a crude product, which was purified by reverse phase preparative HPLC to afford the depicted product (0.015 g, 16%). Mass spec: Calculated 598.3. Observed 599.1

EXAMPLE 3

Hydromorphone 3-(N-methyl-N-(2-N'-acetylarginylamino))ethylcarbamate

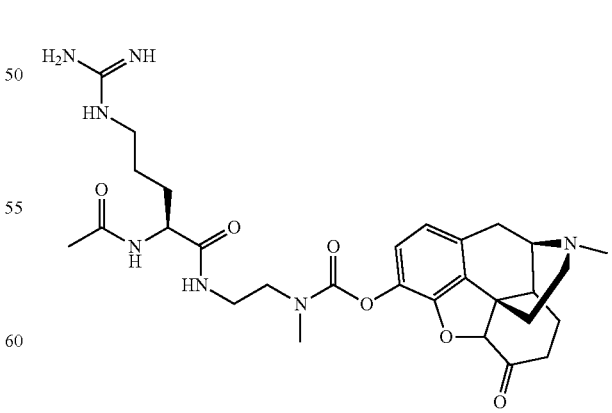

Prepared following the method of Preparation 5 and Example 2, but using acetic anhydride instead of BocGlyOSu. Mass spec: Calculated 583.3. Observed 584.4.

EXAMPLE 4

Hydromorphone 3-(N-methyl-N-(2-N'-t-butanoylarginylamino))ethylcarbamate

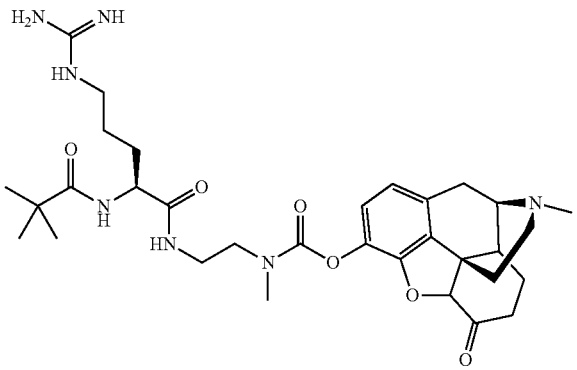

Prepared following the method of Preparation 5 and Example 2, but using t-butanoyl chloride instead of BocGlyOSu. Mass spec: Calculated 625.4. Observed 626.8.

EXAMPLE 5

Hydromorphone 3-(N-methyl-N-(2-N'-benzoylarginylamino))ethylcarbamate

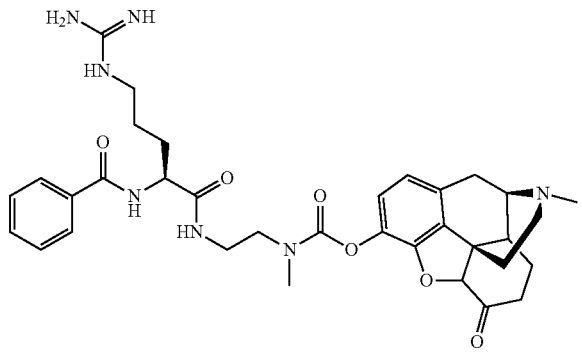

Prepared following the method of Preparation 5 and Example 2, but using benzoyl chloride instead of BocGlyOSu. Mass spec: Calculated 645.3. Observed 646.7.

EXAMPLE 6

Hydromorphone 3-(N-methyl-N—(N'-piperonyl-2-arginylamino))ethylcarbamate

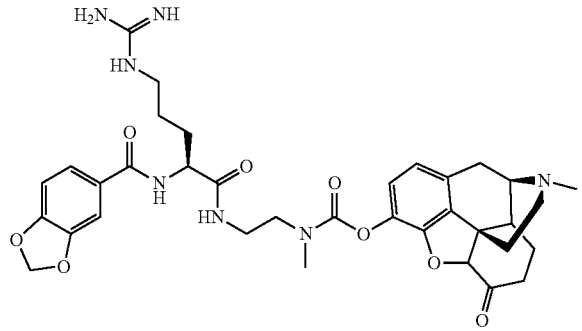

Prepared following the method of Preparation 5 and Example 2, but using piperonyl chloride instead of BocGlyOSu. Mass spec: Calculated 689.3. Observed 690.4.

EXAMPLE 7

Hydromorphone 3-(N-methyl-N-(2-lysinylamino))ethylcarbamate

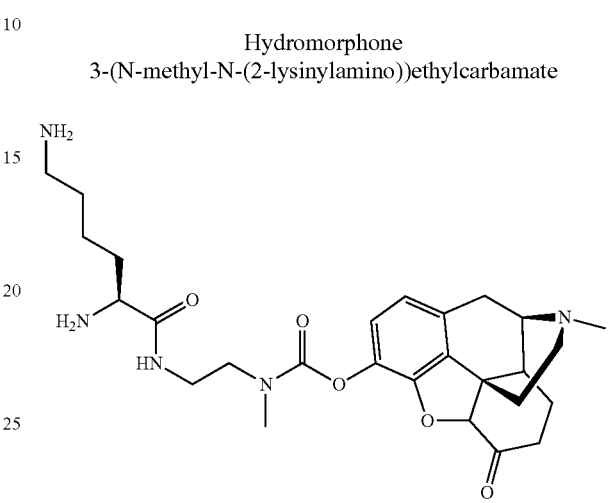

Prepared following the method of Preparations 1 to 4 and Example 1, but using BocLys(Boc)OH instead of BocArg(diBoc)OH. Mass spec: Calculated 513.3. Observed 514.2.

EXAMPLE 8

Hydromorphone 3-(N-methyl-N-(2-lysinyl(methyl)amino))ethylcarbamate

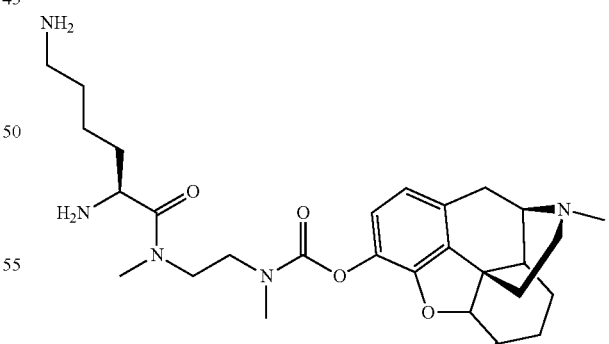

Prepared following the method of Example 7, but using CH$_3$NHCH$_2$CH$_2$N(CH$_3$)CBz instead of H$_2$NCH$_2$CH$_2$N(CH$_3$)CBz. Mass spec: Calculated 527.3. Observed 528.2.

EXAMPLE 9

Hydromorphone 3-(N-methyl-N-(2-arginyl(methyl)amino))ethylcarbamate

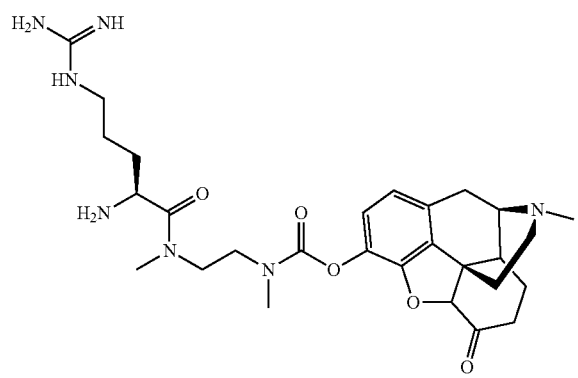

Prepared following the method of Preparations 1 to 4 and Example 1, but using CH₃NHCH₂CH₂N(CH₃)CBz instead of H₂NCH₂CH₂N(CH₃)CBz. Mass spec: Calculated 555.3. Observed 556.3.

EXAMPLE 10

Hydromorphone 3-(N-methyl-N-(2-glutamylamino))ethylcarbamate

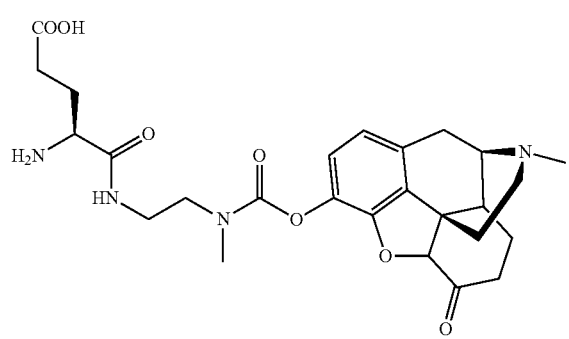

Prepared following the method of Preparations 1 to 4 and Example 1, but using BocGlu(OBuᵗ)OH instead of BocArg(diBoc)OH. Mass spec: Calculated 514.2. Observed 515.3.

EXAMPLE 11

Hydromorphone 3-(N-methyl-N-(2-aspartamylamino))ethylcarbamate

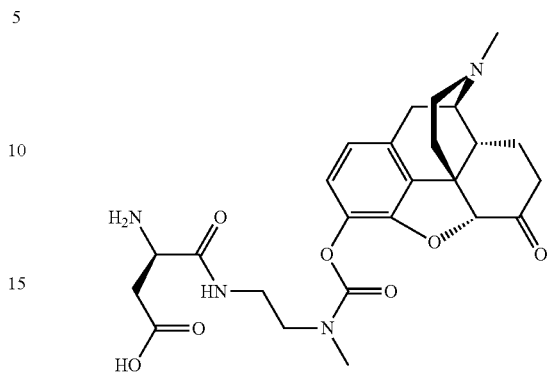

Prepared following the method of Preparations 1 to 4 and Example 1, but using BocAsp(OtBu)OSu instead of BocArg(diBoc)OH. Mass spec: Calculated 500.23. Observed 501.5.

EXAMPLE 12

Hydromorphone 3-(N-methyl-N-(2-tyrosinylamino))ethylcarbamate

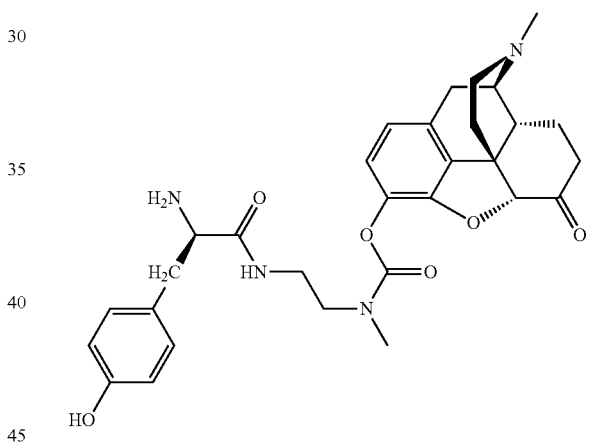

Prepared following the method of Preparations 1 to 4 and Example 1, but using BocTyr(OtBu)OH instead of BocArg(diBoc)OH. Mass spec: Calculated 548.26. Observed 549.3

REFERENCE EXAMPLE 1

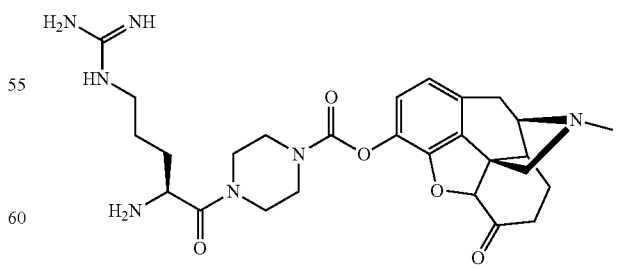

Prepared following the method of Preparations 1 to 4 and Example 1, but using CBzpiperidine instead of H₂NCH₂CH₂N(CH₃)CBz. Mass spec: Calculated 553.3. Observed 554.5.

Preparation 6

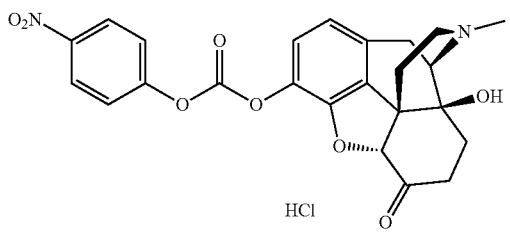

Oxymorphone (0.15 g, 0.5 mmol) was suspended in dichloromethane (3 ml). p-Nitrophenylchlorocarbonate (0.105 g (0.52 mmol) in dichloromethane (5 ml) was then added dropwise over a period of 5 minutes. The reaction mixture was then sonicated for 2 hours to afford a stock solution of the depicted product that was used in the next step.

Preparation 7

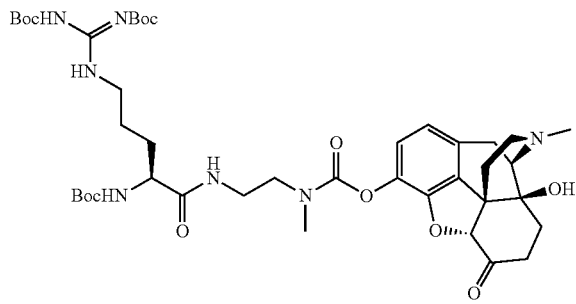

The product of Preparation 2, previously described, (0.265 g, 0.5 mmol) was added to the product of Preparation 6 (stock solution, 8 ml, 0.5 mmol). The pH was then adjusted by adding triethylamine (0.14 ml, 1.0 mmol). The reaction mixture was then stirred for 4 hours. The solvent was then evaporated under a vacuum, and the residue was dissolved in a diethyl ether-ethyl acetate mixture (3:1, 10 ml) and washed four times with 5 ml of 1M aqueous sodium carbonate. The organic layer was then washed three times with water (10 ml) and once with brine (10 ml), then dried over magnesium sulfate. The solvent was then removed by evaporation to afford the depicted product 0.39 g (90%).

EXAMPLE 13

Oxymorphone 3-(N-methyl-N-(2-arginylamino))ethylcarbamate

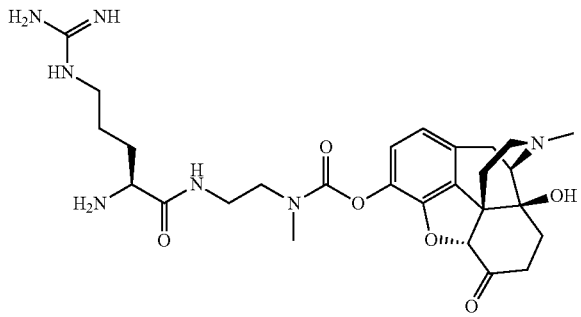

The product of Preparation 7 (0.39 g, 0.46 mmol) was dissolved in a 1:1 mixture of dichloromethane and trifluoroacetic acid (6 ml). The reaction mixture was then stirred for 6 hours. The solvent was then removed by evaporation under a vacuum, and the residue was triturated with ethyl ether (10 ml). A precipitate formed, and this was filtered off, washed with diethyl ether (10 ml) four times and dried in a stream of dry nitrogen gas to afford a crude product (0.46 g). A portion of the crude product (0.06 g) was purified by reverse phase preparative HPLC (acetonitrile gradient) to afford the depicted compound (0.035 g, 90%). Mass spec: Calculated 557.3. Observed 558.0

Preparation 8

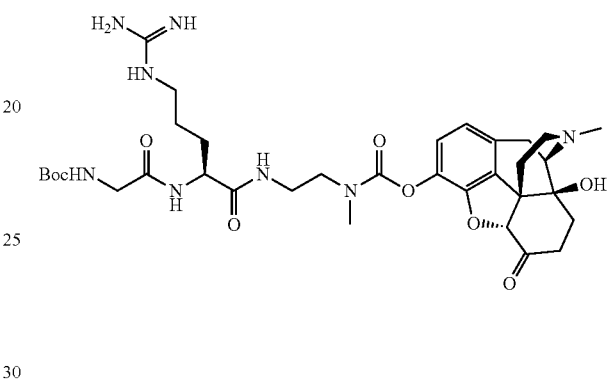

BocGlyOSu (0.065 g, 0.24 mmol) was added to a stirred solution of the crude product of Example 13 (0.2 g, 0.22 mmol) in dimethylformamide (3 ml). Triethylamine (0.066 ml, 0.48 mmol) was then added to the reaction mixture and the resulting solution was stirred for 2 hours. The solvent was then removed by evaporation under a high vacuum, and the residue was triturated with diethyl ether (three times by 3 ml) to afford the depicted compound (0.164 g, 79%).

EXAMPLE 14

Oxymorphone 3-(N-methyl-N-(2-N'-glycinylarginylamino))ethylcarbamate

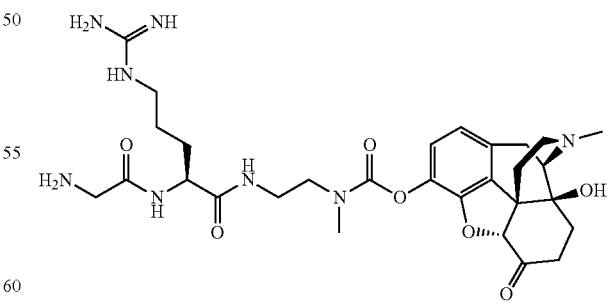

The product of Preparation 8 was deprotected following the method of Example 13 to afford a crude product, which was purified by reverse phase preparative HPLC to afford the depicted product (0.055 g, 44%). Mass spec: Calculated 614.3. Observed 615.4.

EXAMPLE 15

Oxymorphone 3-(N-methyl-N-(2-N'-acetylarginy-lamino))ethylcarbamate

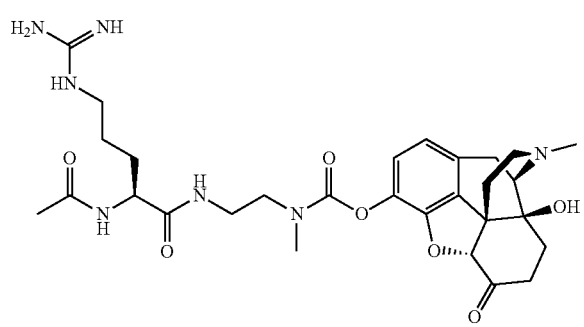

Prepared and purified following the method of Preparation 8 and Example 14, but using acetic anhydride instead of BocGlyOSu. Mass spec: Calculated 599.3. Observed 600.4.

Preparation 9

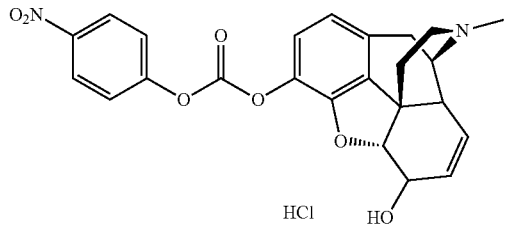

The product of Preparation 9 was synthesized following the method of Preparation 7, substituting morphine for oxymorphone, to afford a stock solution of the depicted product that was used in preparation 10.

Preparation 10

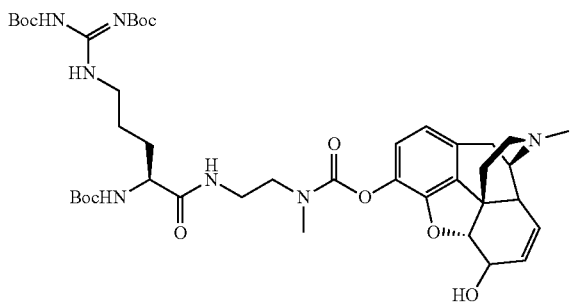

The product of Preparation 10 was synthesized following the method of Preparation 12 to afford the depicted product 0.85 g (92%).

EXAMPLE 16

MMorphine 3-(N-methyl-N-(2-arginylamino))ethylcarbamate

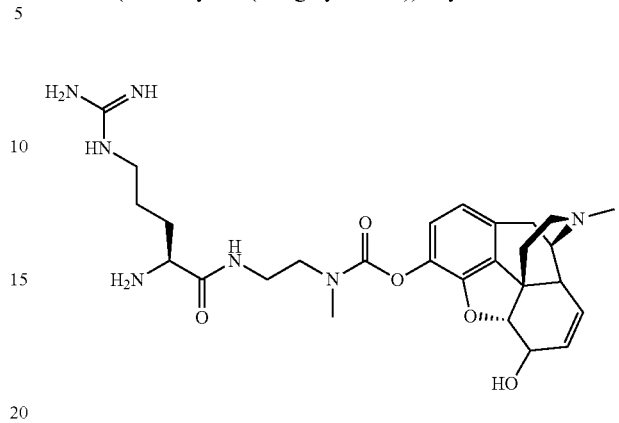

The product of Example 16 was synthesized following the method of Example 13 to afford a crude product (0.93 g). A portion of the crude product (0.08 g) was purified by reverse phase preparative HPLC (acetonitrile gradient) to afford the depicted compound (0.043 g, 45%). Mass spec: Calculated 541.6 Observed 542.6

Preparation 11

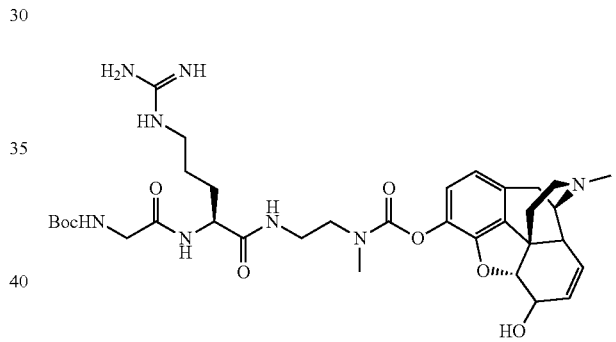

The product of Preparation 11 was synthesized following the method of Preparation 13 to afford the depicted compound (0.18 g, 84%).

EXAMPLE 17

Morphine 3-(N-methyl-N-(2-N'-glycinylarginy-lamino))ethylcarbamate

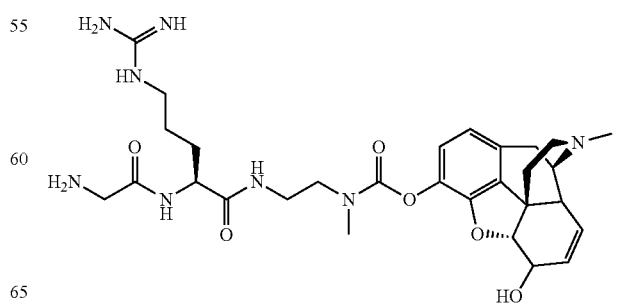

The product of Preparation 11 was deprotected following the method of Example 13 to afford a crude product, which was purified by reverse phase preparative HPLC to afford the depicted product (0.036 g, 40%). Mass spec: Calculated 598.7. Observed 599.6.

EXAMPLE 18

Morphine 3-(N-methyl-N-(2-N'-acetylarginylamino)) ethylcarbamate

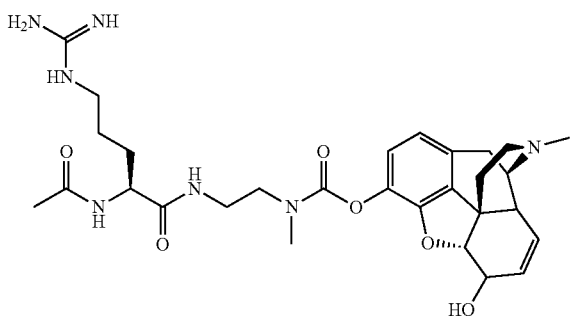

Prepared and purified following the method of Preparation 8 and Example 14, but using acetic anhydride instead of BocGlyOSu. Mass spec: Calculated 583.7. Observed 584.5.

Preparation 12

Naltrexone free base was prepared according to protocol similar to that described in U.S. Pat. No. 4,176,186.

(R)—N-methylnaltrexone was synthesized according to a protocol similar to that described in WO2006127899.

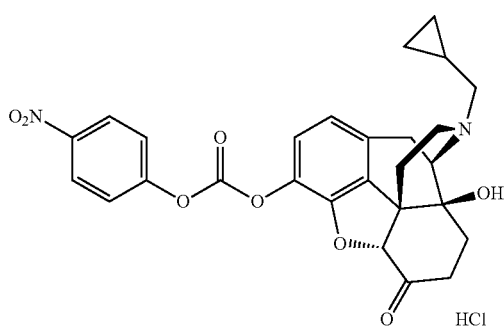

Naltrexone (0.34 g (1.0 mmol)) was dissolved in dichloromethane (10 ml). p-Nitrophenylchlorocarbonate (0.212 g (1.1 mmol) in dichloromethane (5 ml) was then added dropwise over a period of 5 minutes. The reaction mixture was then sonicated for 2 hours to afford a stock solution of the depicted product that was used in the next step.

Preparation 13

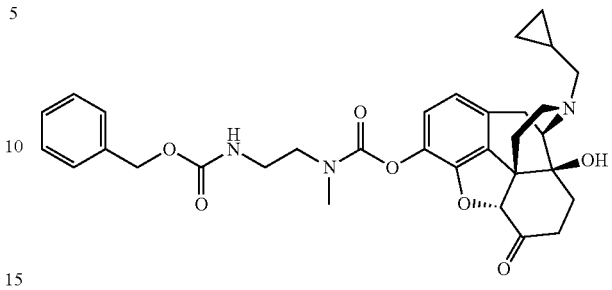

The product of Preparation 12 (stock solution, 15 ml, 1.0 mmol) was added to the solution of 0.265 g (1.05 mmol) of benzyl 2-(methylamino)ethylcarbamate hydrochloride in 10 ml of dimethylformamide. The pH was then adjusted by adding triethylamine (0.28 ml, 2.0 mmol). The reaction mixture was then stirred for 2 hours. The solvent was then evaporated under a vacuum, and the residue was dissolved in ethyl acetate (20 ml) and washed four times with 10 ml of 1M aqueous sodium carbonate. The organic layer was then washed three times with water (10 ml) and once with brine (10 ml), then dried over magnesium sulfate. The solvent was then removed by evaporation to afford the depicted product 0.425 g (74%). Mass spec: Calculated 575.26 Observed 576.4.

Preparation 14

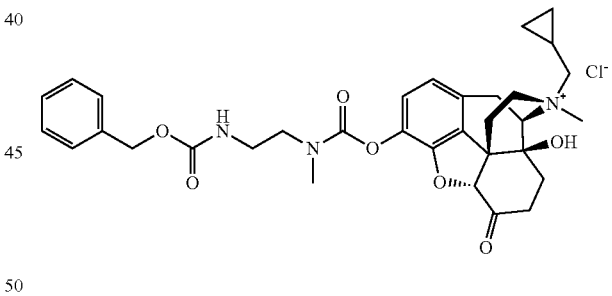

The product of Preparation 13 (0.425 g, 0.74 mmol) was dissolved in 5 ml of dry acetone. Methyl iodide (1.42 g, 10 mmol) was added and the mixture was heated in a capped tube at 85° C. for 3 days. The solvent was then removed by evaporation. The residue was then dissolved in 10 ml of methanol and loaded onto a column with 4 g of anion-exchange resin, chloride form (DOWEX 1×2-200). The chloride salt was eluted from the column using 50 ml of methanol. The solution was then evaporated to 10 ml volume and mixed with 2 g of silica gel. The remaining solvent was then evaporated and the residual dry powder was loaded onto a silica gel column. Remaining starting compound was then eluted with dichloromethane/1M solution of ammonia in methanol (95:5). The product was then eluted with dichloromethane/1M solution of ammonia in methanol (70:30) to afford the depicted compound 0.125 g (27%).

EXAMPLE 19

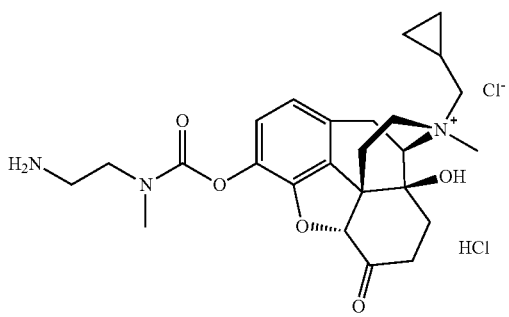

The product of Preparation 14 (0.125 g, 0.2 mmol) was dissolved in trifluoroacetic acid (3 ml). A 1 M solution of boron tribromide in dichloromethane (0.4 ml, 0.4 mmol) was added at 0-5° C. The mixture was then stirred for 2 hours. The solvent was removed in vacuum. 10 ml of 3 N aqueous hydrogen chloride were mixed with the residue and the mixture was stirred for 16 hours. After evaporation of water under a vacuum, the crude product was purified by reverse phase preparative HPLC (acetonitrile gradient) to afford the depicted compound (0.032 g, 30%). Mass spec: Calculated 456.25. Observed 456.4.

Preparation 15

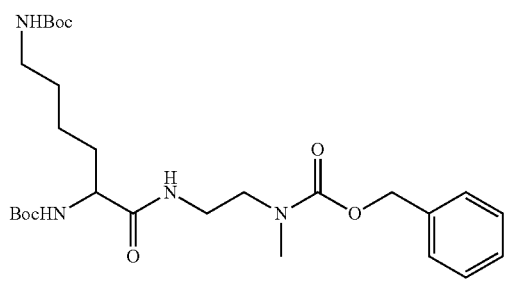 [SMILES: CN(CCNC(=O)C(CCCCNC(=O)OC(C)(C)C)NC(=O)OC(C)(C)C)C(=O)OCc1ccccc1]

The product of Preparation 15 was prepared following the method of Preparation 1, but using BocLys(Boc)OH to afford depicted product with 74% yield.

Preparation 16

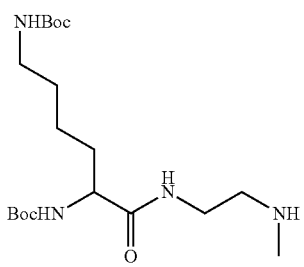 [SMILES: CNCCNC(=O)C(CCCCNC(=O)OC(C)(C)C)NC(=O)OC(C)(C)C]

The product of Preparation 16 was prepared following the method of Preparation 2 using the product of Preparation 15 to afford depicted product with 95% yield.

Preparation 17

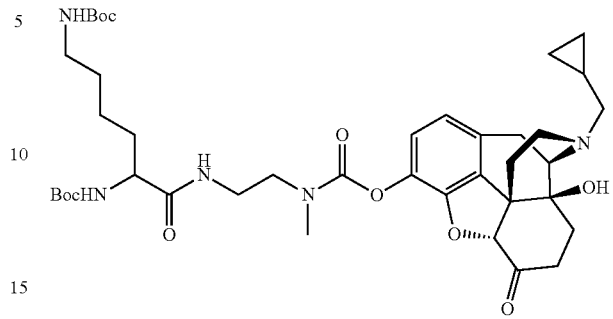

The product of Preparation 17 was prepared following the method of Preparation 12, but using the product of Preparation 16a to afford the depicted product with 66% yield.

Preparation 18

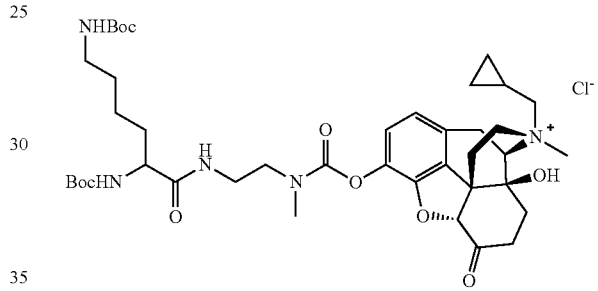

Prepared following the method of Preparation 14. Yield 16%.

EXAMPLE 20

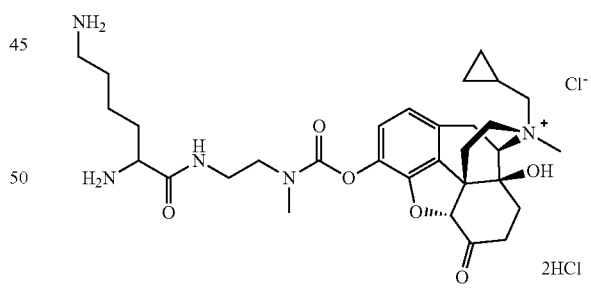

Prepared following the method of Example 1. The crude product was purified by reverse phase preparative HPLC (acetonitrile gradient) to afford the depicted compound (33%). Mass spec: Calculated 584.3. Observed 584.5.

Protocols for Evaluating Test Compounds

1a. "Kitchen" Test

The stability of a test compound in the presence of the readily available household chemicals, acetic acid (vinegar) and sodium bicarbonate (baking soda) may be demonstrated in the following "Kitchen" Test.

0.5 mg of a test compound is dissolved in 1 ml of each of the following solutions corresponding with possible household chemicals: 30% aqueous acetic acid; 50% aqueous ethanol and saturated aqueous solution of sodium bicarbonate (baking soda). Each solution is kept at room temperature for 20-24 hours and then heated at 85° C. for 20-24 hours. Hydromorphone release and general stability are monitored by analytical HPLC. A compound is considered as having passed this test if after 20 hours the hydromorphone concentration does not exceed 10% of the starting material or other product of degradation.

The compounds exemplified herein have passed this test.

1b. Demonstration of the Controlled Release of Parent Drug from "Activated" Prodrugs.

In Vitro Demonstration

The controlled release of parent drug (e.g. hydromorphone) from the prodrug was demonstrated by the synthesis, and in vitro testing of several compounds depicted in Table 1. Compounds A, and C are examples of "activated" prodrugs whereby the enzyme-cleavable activating group has been omitted to enable specific evaluation of the kinetics attending the intramolecular cyclization-release sequence. As previously described, the intramolecular cyclization-release sequence results in the concomitant formation of a cyclic urea with the release of the parent drug.

These release kinetics of these compounds were evaluated in aqueous solutions at increasing pH. The liberation of hydromorphone during the course of these reactions was confirmed by LC-MS analysis. Compound D is an interesting example of a molecule that bears a nucleophilic nitrogen atom, yet it is rendered incapable of undergoing the intramolecular cyclization-release reaction due to the conformational restrictions imposed by the cyclic piperazine ring (i.e it cannot adopt the conformation required for the nucleophilic addition of the lone pair of electrons on nitrogen into the carbonyl carbon of the carbamate moiety). A further example of the structural features required for the intramolecular cyclization-release reaction is provided by compound B representing a molecule is in its "unactivated" form (i.e. the lone pair of electrons on the now acylated nitrogen atom are unavailable for nucleophilic attack on the carbamate). It is interesting to note that the intramolecular cyclization-release reactions can be suppressed at low pH by deactivation of the nucleophilic nitrogen atom via protonation.

These data confirm the functional roles of the spacer and the "activated" nucleophilic nitrogen in the intramolecular cyclization-release of the parent drug molecule.

TABLE 1

The liberation of hydromorphone from prodrug in aqueous solutions.

| Structure | % production of hydromorphone 20 hrs | | | cpd. |
|---|---|---|---|---|
| | pH 7.5 | 10 | 11.5 | |
| [structure with 2HCl] | 10 | 100 | 100 | A |
| [structure with HCl] | 0 | 0 | 5 | B |
| [structure with 2HCl] | 90 | 100 | 100 | C |

TABLE 1-continued

The liberation of hydromorphone from prodrug in aqueous solutions.

| Structure | % production of hydromorphone 20 hrs | | | cpd. |
|---|---|---|---|---|
| | pH 7.5 | 10 | 11.5 | |
| [structure: piperazine carbamate of hydromorphone, 2HCl] | 0 | 0 | 0 | D |

In Vivo Demonstration

In order to investigate the formation of parent drug form prodrug in vivo, compounds depicted in Table 2 were synthesized and administered intravenously to rats. Subsequent to dosing, plasma levels of hydromorphone were measured as described in the experimental section. Compounds A, and B are examples of "activated" prodrugs whereby the enzyme-cleavable activating group has been omitted to enable specific evaluation of the kinetics attending the intramolecular cyclization-release sequence As previously described, the intramolecular cyclization-release sequence results in the concomitant formation of a cyclic urea with the release of the parent drug.

When these drugs are administered to rats, hydromorphone is liberated. Compound C is an interesting example of a molecule that bears a nucleophilic nitrogen atom, yet it is rendered incapable of undergoing the intramolecular cyclization-release reaction due to the conformational restrictions imposed by the cyclic piperazine ring (i.e it cannot adopt the conformation required for the nucleophilic addition of the lone pair of electrons on nitrogen into the carbonyl carbon of the carbamate moiety). When this compound is administered to rats, no hydromorphone is detected. Compound D is an example of a prodrug whereby the enzyme-cleavable protecting group has been attached to a piperazine nitrogen. This molecule was studied to assess the possibility of a direct enzyme-mediated hydrolysis of the carbamate moiety. The data indicates that this process does not occur in vivo. Interestingly, when Compound D is administered to rats Compound C is formed and no hydromorphone is liberated, thus also providing further evidence for the in vivo "activation" of the described prodrugs.

TABLE 3

The liberation of hydromorphone from prodrugs following IV administration in rats.

| Structure | | Cmax HM (ng/ml) following IV dosing |
|---|---|---|
| [structure A: N-methyl-N-(2-aminoethyl) carbamate of hydromorphone, 2HCl] | A | 1050 |
| [structure B: N-methyl-N-(2-(methylamino)ethyl) carbamate of hydromorphone, 2HCl] | B | 204 |
| [structure C: piperazine carbamate of hydromorphone, 2HCl] | C | 0 |

TABLE 3-continued

The liberation of hydromorphone from prodrugs following IV administration in rats.

| Structure | | Cmax HM (ng/ml) following IV dosing |
|---|---|---|
| 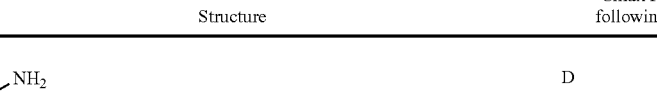 | D | 0 |

2. In Vitro Human µ-Opioid Receptor Binding Assay.

This test measures the affinity of test compounds for the µ-opioid receptor relative to hydromorphone.

General Procedure:

The general procedure follows the protocol described by Wang, J.-B., Johnson, P. S., Perscio, A. M., Hawkins, A. L., Griffin, C. A. and Uhl, G. R. (1994). FEBS Lett., 338: 217-222.

Assay: α-opioid receptor
Origin: human recombinant (HEK-293 cells)
Reference compound: [d-Ala$^2$,N-Me-Phe$^4$,Gly$^{5-}$ol]-enkephalin (DAMGO)
Radioligand: [$^3$H]DAMGO (0.5 nM)
Non-specific ligand: naloxone (10 uM)
Incubation: 120 min @ 22° C.
Method of detection: scintillation counting Analysis and Expression of Results:

The specific binding to the receptors is defined as the difference between the total binding and the non-specific binding determined in the presence of an excess of unlabelled ligand. The results are expressed as a percent of control of specific binding and as a present inhibition of control specific binding obtained in the presence of test compounds. The IC$_{50}$ values (molar concentration causing a half-maximal inhibition of control specific binding), and Hill coefficients (nH) were determined by non-linear regression analysis of competition curves using Hill equation curve fitting.

Results:

TABLE 4

| Example | IC$_{50}$ HUMAN µ-opioid receptor |
|---|---|
| Hydromorphone HCl (HM) | 1E−09 |
| 7 | 7.9E−07 |
| 1 | 2.1E−06 |
| 3 | 1.3E−06 |
| 6 | 7.9E−07 |

The above results are consistent with the structure activity relationships for opioids obtained in the literature, obtained from screening of these representative molecules, demonstrate the deactivation of opioid potency when the promoiety is appended to the phenol residue of hydromorphone.

3. Pharmacokinetic Data

Plasma Timecourse of Hydromorphone Following IV Administration to Rat

IV dosing: Test compound is dissolved in saline (2 mg/ml) and injected into the tail vein of jugular vein cannulated male Sprague-Dawley rats. Hydromorphone (HM) at 1 mg/kg, oxyydromorphone (OM) at 0.5 mg/kg, morphine (MR) at 1 mg/kg, and N-methylnaltrexone (N-MTX) at 2 mg/kg are used as positive controls, and the test compounds are dosed at a parent opioid equivalent dose (e.g. equal to 1 mg/kg, 0.5 mg/kg or 2 mg/kg). At specified time points, blood is withdrawn, quenched into methanol, centrifuged at 14000 rpm @ 4° C., and stored at −80° C. until analysis. Samples are quantified via LC/MS/MS using an ABI 3000 triple-quad mass spectrometer.

Oral dosing: The test compound is dissolved in saline (20 mg/ml) and dosed via oral gavage into jugular vein cannulated male Sprague-Dawley rats. HM, OM, MR and 10 mg/kg, and N-MTX at 20 mg/kg are used positive controls and the test compound is dosed at an approximate parent opioid equivalent dose (e.g. equal to 10 or 20 mg/kg). At specified time points, blood is withdrawn, quenched into methanol, centrifuged at 14000 rpm @ 4° C., and stored at −80° C. until analysis. Samples are quantified via LC/MS/MS using an ABI 3000 triple-quad mass spectrometer.

Results:

TABLE 5

Maximum concentration (Cmax) of hydromorphone (HM) found in blood after IV dosing in rats.

| Example | Cmax HM (ng/ml) following IV dosing |
|---|---|
| hydromorphone | 352 |
| 7 | 208 |
| 8 | 17 |
| 1 | 55 |
| 3 | 17 |
| 9 | 231 |
| 6 | 3 |
| 2 | 78 |
| 11 | 33 |
| 12 | 48 |

TABLE 6

Maximum concentration of hydromorphone (HM) found
in blood after oral (PO) dosing in rats.

| Example | Cmax HM (ng/ml) following PO dosing |
|---|---|
| hydromorphone | 45 |
| 7 | 44 |
| 3 | 11 |
| 2 | 35 |
| 6 | 18 |
| 11 | 34 |
| 12 | 21 |

Compared to hydromorphone, compounds according to the invention afford a lower Cmax of hydromorphone when administered IV, but demonstrate similar Cmax values to hydromorphone when administered orally.

TABLE 7

Maximum concentration (Cmax) of oxymorphone
(OM) found in blood after IV dosing in rats.

| Example | Cmax OM (ng/ml) following IV dosing |
|---|---|
| oxymorphone | 432 |
| 13 | 303 |
| 14 | 205 |
| 15 | 4 |

TABLE 8

Maximum concentration of oxymorphone (OM) found
in blood after oral (PO) dosing in rats.

| Example | Cmax OM (ng/ml) following PO dosing |
|---|---|
| oxymorphone | 7.8 |
| 13 | 7.8 |
| 14 | 15.5 |
| 15 | 13.3 |

Compared to oxymorphone, compounds according to the invention afford a lower Cmax of oxymorphone when administered IV, but demonstrate similar Cmax values to oxymorphone when administered orally.

TABLE 9

Maximum concentration (Cmax) of morphine (MR)
found in blood after IV dosing in rats.

| Example | Cmax MR (ng/ml) following IV dosing |
|---|---|
| morphine | 111.5 |
| 17 | 57.7 |
| 18 | 0 |

TABLE 10

Maximum concentration of morphine (MR) found
in blood after oral (PO) dosing in rats.

| Example | Cmax MR (ng/ml) following PO dosing |
|---|---|
| morphine | 41.7 |
| 17 | 23.7 |
| 18 | 55.2 |

Compared to morphine, compounds according to the invention afford a lower Cmax of morphine when administered IV, but demonstrate similar Cmax values to morphine when administered orally.

TABLE 11

Maximum concentration of (R)-N-methylnaltrexone (N-
MTX) found in blood after oral (PO) dosing in rats.

| Example | Cmax N-MTX (ng/ml) following PO dosing |
|---|---|
| N-methylnaltrexone | 6 |
| 19 | 71 |

Note:
Unlike the previous prodrug examples, which were dosed at equimolar concentrations, these compounds were dosed at equal masses (20 mg/kg).

The compound of Example 19, which is a secondary carbamate prodrug of (R)—N-Methylnaltexone, describes one aspect of the invention which embodies a method of providing a patient with post administration-activated, controlled release of a phenolic opioid antagonist, in this case a peripherally active opioid antagonist. Compared to (R)—N-methylnaltrexone, the compound affords a superior Cmax value compared to (R)—N-methylnaltrexone when administered orally.

FIG. 1. Plasma concentration time course of the production of N-MTX following oral (PO) dosing in rats. The solid line represents the plasma concentration of N-MTX following PO dosing of N-MTX at 20 mg/kg. The dashed line represents the plasma concentration of N-MTX produced following oral dosing of Example 19 at 20 mg/kg.

Figure 2:
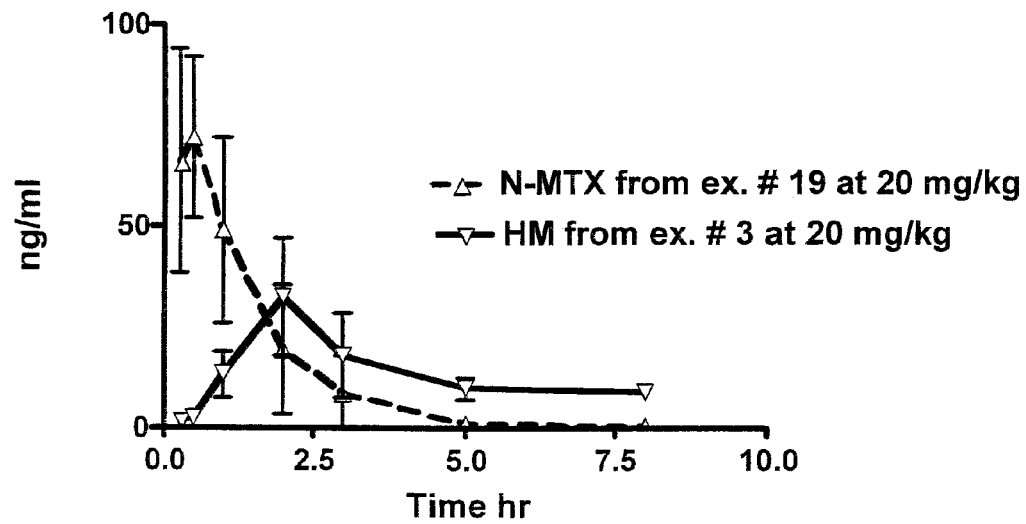
FIG. 2 shows the plasma concentration time course of the production of hydromorphone and N-MTX following PO dosing of prodrugs in rats.

FIG. 2. Plasma concentration time course of the production of hydromorphone and N-MTX following PO dosing of prodrugs in rats. The solid line represents the plasma concentration of hydromorphone following PO dosing of Example 3 at 10 mg/kg. The dashed line represents the plasma concentration of N-MTX following oral dosing of Example 19 at 20 mg/kg.

By examining the plasma time course represented by FIG. 1 it is clear that the utility of (R)—N-methylnaltrexone may be limited by its poor pharmacokinetic profile (e.g. oral bioavailability). This limitation can be overcome by the prodrug represented by the compound of Example 19 which provides an improved pharmacokinetic profile (e.g. increased oral bioavailabilty). Furthermore FIG. 2 demonstrates that the prodrug approach represented by the compounds of Examples 3 and 19 allows for higher, and perhaps complimentary, plasma levels of opioid agonist and antagonist to be obtained when prodrugs thereof are dosed orally.

Plasma Timecourse of Hydromorphone Following IV Administration in Dog.

Fifteen male beagle dogs were selected from the Test Facility's colony of non-naïve animals and placed into five groups of three animals per group. The animals were assigned to the study based on acceptable health as determined by a staff veterinarian following a pre-study health status check. The animals were fasted overnight prior to each dosing session and food was returned to the animals approximately 4 hours post-dose for each dose session. All substances were stored at 22±5° C. prior to dosing under desiccate conditions.

Intravenous Administration.

The test compounds were prepared in 0.9% NaCl at a target concentration of 0.4 mg/mL (0.4 mg/kg final dose) for intravenous administration. Hydromorphone was prepared in 0.9% NaCl at a target concentration of 0.2 and 0.1 mg/m (0.1 and 0.2 mg/kg final dose) for intravenous administration.

A dose formulation sample (0.15 mL) was collected from each intravenous formulation, prior to dosing, pre- and post-filtration. All dose formulation samples were stored at −20±5° C. until analyzed.

Test compounds were administered through a temporary percutaneous catheter placed in a peripheral vein at a target dose level of 0.4 mg/kg and a dose volume of 1 mL/kg. The Animals received a slow intravenous bolus push over a 1.5 minute period. Hydromorphone was administered similarly at a target dose level of 0.2 mg/kg and a dose volume of 1 mL/kg. The animals received a slow intravenous bolus push over a 2 minute period. Immediately following intravenous dosing, the catheters were flushed with 3 mL of saline prior to removal. Blood samples (0.5 mL, whole blood, Li-Heparin anticoagulant) were collected prior to dosing and at timepoints up to 24 hours following intravenous dosing. All samples were collected via direct venipuncture of a peripheral vein, quenched into methanol, centrifuged at 14000 rpm @ 4° C., and stored at −80° C. until analysis. Samples are quantified via LC/MS/MS using an ABI 3000 triple-quad mass spectrometer.

Oral Administration.

The test compounds were prepared in 0.9% NaCl at a target concentration of 4 mg/mL (4 mg/kg final dose) for oral administration. Hydromorphone, was prepared in 0.9% NaCl at a target concentration of 2 mg/mL (2 mg/kg final dose) for oral administration. The oral formulations were mixed by swirling and sonicated as needed to aid in complete dissolution. A dose formulation sample (0.15 mL) was collected from each oral formulation prior to dosing. All dose formulation samples were stored at −20±5° C. until analyzed. Test compounds were administered via oral gavage at a target dose level 4 mg/kg and at a dose volume of 1 mL/kg. Hydromorphone was administered via oral gavage at a target dose level 2 mg/kg and at a dose volume of 1 mL/kg. Immediately following oral dosing the gavage tubes were flushed with 10 mL of water prior to removal. Blood samples (0.5 mL, whole blood, Li-Heparin anticoagulant) were collected prior to dosing and at timepoints up to 24 hours following oral dosing. All samples were collected via direct venipuncture of a peripheral vein quenched into methanol, centrifuged at 14000 rpm @ 4° C., and stored at −80° C. until analysis. Samples are quantified via LC/MS/MS using an ABI 3000 triple-quad mass spectrometer.

Results:

TABLE 12

Maximum concentration (Cmax) of hydromorphone (HM) found in blood after IV dosing in dogs.

| Example | Cmax HM (ng/ml) following IV dosing |
|---|---|
| Hydromorphone | 55.7 |
| 2 | 34.3 |
| 3 | 0 |
| 6 | 17.2 |

TABLE 13

Maximum concentration of hydromorphone (HM) found in blood after oral (PO) dosing in dogs.

| Example | Cmax HM (ng/ml) following PO dosing |
|---|---|
| Hydromorphone | 58.2 |
| 2 | 35.8 |
| 3 | 55.9 |
| 6 | 21.8 |

Compared to hydromorphone, compounds according to the invention afford a lower Cmax of hydromorphone when administered IV, but demonstrate similar Cmax values to hydromorphone when administered orally.

Taken together, these test data demonstrate that compounds according to the invention are capable of providing patients with post administration-activated, controlled release of a phenolic opioid. In particular, the data demonstrate that the pro-drugs release opioid when administered orally, but resist release of opioid when subjected to conditions commonly used by those who wish to abuse the drug.

The invention claimed is:

1. A method of treating or preventing pain comprising administering to a patient in need thereof an effective amount of a compound of structural Formula (I):

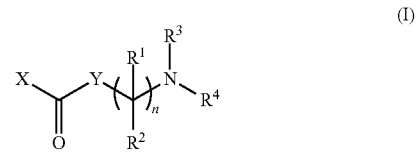

or a pharmaceutically acceptable salt thereof wherein:

X is a phenolic opioid agonist, wherein the hydrogen atom of the phenolic hydroxyl group is replaced by a covalent bond to —C(O)—Y—(C(R$^1$)(R$^2$))$_n$—N—(R$^3$)(R$^4$);

Y is —NR$^5$— and R$^5$ is (1-4C)alkyl;

n is 2 or 3;

R$^1$ and R$^2$ are each hydrogen;

R$^3$ is hydrogen or (1-4C)alkyl; and

R$^4$ is a residue of an L-amino acid selected from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; a residue of a dipeptide composed of two L-amino acid residues or a tripeptide composed of three L-amino acid residues, wherein the amino acids are selected independently from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; or a residue of an N-acyl derivative thereof.

2. The method of claim 1, wherein X is hydromorphone, oxymorphone, or morphine.

3. The method of claim 1, wherein X is hydromorphone.

4. The method of claim 1, wherein X is morphine.

5. The method of claim 1, wherein X is oxymorphone.

6. The method of claim 1, in which R$^5$ is methyl.

7. The method of claim 1, in which R$^5$ is ethyl.

8. The method of claim 1, in which R$^3$ is hydrogen or methyl.

9. The method of claim 1, in which R$^3$ is hydrogen.

10. The method of claim 1, in which R$^4$ is a residue of an L-amino acid selected from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine.

11. The method of claim 1, in which R$^4$ is a residue of an N-acyl derivative of an L-amino acid selected from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine.

12. The method of claim 1, in which $R^4$ is a residue of arginine, N-acetylarginine, N-t-butanoylarginine, N-benzoylarginine, N-piperonylarginine, N-glycinylarginine, lysine, N-acetyllysine, glutamic acid, aspartic acid, tyrosine, proline or N-glycinylproline.

13. The method of claim 12, in which $R^4$ is a residue of arginine, N-acetylarginine, N-t-butanoylarginine, N-benzoylarginine, N-piperonylarginine, N-glycinylarginine, lysine, glutamic acid, proline or N-glycinylproline.

14. The method of claim 12, in which $R^4$ is a residue of arginine or N-acetylarginine.

15. The method of claim 12, in which $R^4$ is a residue of lysine or N-acetyllysine.

16. The method of claim 1, wherein the compound is hydromorphone 3-(N-methyl-N-(2-N'-acetylarginylamino))ethylcarbamate, or a pharmaceutically acceptable salt thereof.

17. The method of claim 1, wherein the compound is morphine 3-(N-methyl-N-(2-N'-acetylarginylamino))ethylcarbamate, or a pharmaceutically acceptable salt thereof.

18. The method of claim 1, wherein the compound is oxymorphone 3-(N-methyl-N-(2-N'-acetylarginylamino))ethylcarbamate, or a pharmaceutically acceptable salt thereof.

* * * * *